United States Patent
Eitan et al.

(10) Patent No.: US 12,318,576 B2
(45) Date of Patent: Jun. 3, 2025

(54) INFUSION PUMP WITH TOGGLING CAPABILITY

(71) Applicant: EITAN MEDICAL LTD., Netanya (IL)

(72) Inventors: Shaul Eitan, Hofit (IL); Boaz Eitan, Hofit (IL); Amir Rasowsky, Yakir (IL)

(73) Assignee: EITAN MEDICAL LTD., Netanya (IL)

( * ) Notice: Subject to any disclaimer, the term of this patent is extended or adjusted under 35 U.S.C. 154(b) by 947 days.

(21) Appl. No.: 17/462,495

(22) Filed: Aug. 31, 2021

(65) Prior Publication Data

US 2021/0386931 A1  Dec. 16, 2021

Related U.S. Application Data

(63) Continuation of application No. PCT/IL2020/050246, filed on Mar. 4, 2020.
(Continued)

(51) Int. Cl.
*A61M 5/168* (2006.01)
*A61M 5/142* (2006.01)

(52) U.S. Cl.
CPC .... *A61M 5/16859* (2013.01); *A61M 5/14216* (2013.01); *A61M 5/16813* (2013.01);
(Continued)

(58) Field of Classification Search
CPC .......... A61M 5/16859; A61M 5/16854; A61M 5/16831; A61M 5/14216; A61M 5/16813;
(Continued)

(56) References Cited

U.S. PATENT DOCUMENTS 3,379,950 A   4/1968  Friedline
4,236,880 A  12/1980  Archibald
(Continued)

FOREIGN PATENT DOCUMENTS

CN   103727021   4/2014
EP     0182502   5/1986
(Continued)

OTHER PUBLICATIONS

An Office Action dated Sep. 30, 2019, which issued during the prosecution of U.S. Appl. No. 15/740,365.
(Continued)

*Primary Examiner* — Laura A Bouchelle
*Assistant Examiner* — Sarah Dympna Grasmeder
(74) *Attorney, Agent, or Firm* — Sughrue Mion, PLLC

(57) ABSTRACT

An infusion pump includes upstream and downstream valves, a pressing surface disposed between the valves which presses on an infusion tube, a pressure sensor which measures pressure within the infusion tube, and a controller. In response to the pressure, the controller determines that there is an occlusion in the infusion tube downstream of the downstream valve, and in response thereto, toggles the upstream valve and the downstream valve. The toggling includes sequentially, (a) while the upstream valve remains closed, isolating a segment of the infusion tube between the valves by closing the downstream valve, (b) while the downstream valve remains closed, reducing pressure in the isolated segment by opening the upstream valve, (c) while the downstream valve remains closed, closing the upstream valve, and (d) while the upstream valve remains closed, reducing pressure downstream of the downstream valve by opening the downstream valve. Other applications are also described.

20 Claims, 9 Drawing Sheets

Related U.S. Application Data

(60) Provisional application No. 63/075,341, filed on Sep. 8, 2020, provisional application No. 62/813,897, filed on Mar. 5, 2019.

(52) U.S. Cl.
CPC ............. *A61M 2005/16868* (2013.01); *A61M 2205/18* (2013.01)

(58) Field of Classification Search
CPC .......... A61M 5/16804; A61M 5/16881; A61M 5/16877; A61M 5/16809; A61M 2005/16868; A61M 2005/16863; A61M 2205/18
See application file for complete search history.

(56) References Cited

U.S. PATENT DOCUMENTS

| | | | |
|---|---|---|---|
| 4,322,668 A | 3/1982 | Trussler et al. | |
| 4,391,600 A | 7/1983 | Archibald | |
| 4,650,469 A | 3/1987 | Berg et al. | |
| 5,018,945 A | 5/1991 | D'Silva | |
| 5,049,047 A | 9/1991 | Polaschegg et al. | |
| 5,096,385 A | 3/1992 | Georgi et al. | |
| 5,116,203 A * | 5/1992 | Natwick | A61M 5/16854 417/474 |
| 5,340,951 A | 8/1994 | Hungerbuhler et al. | |
| 5,567,119 A | 10/1996 | Johnson et al. | |
| 5,807,075 A | 9/1998 | Jacobsen et al. | |
| 5,807,322 A * | 9/1998 | Lindsey | A61M 5/16859 604/65 |
| 5,827,223 A * | 10/1998 | Butterfield | A61M 5/16859 604/65 |
| 5,843,035 A | 12/1998 | Bowman et al. | |
| 6,312,227 B1 | 11/2001 | Davis | |
| 6,494,864 B1 | 12/2002 | Kerwin et al. | |
| 6,523,414 B1 | 2/2003 | Malmstrom et al. | |
| 6,531,708 B1 | 3/2003 | Malmstrom et al. | |
| 6,554,806 B2 | 4/2003 | Butterfield et al. | |
| 6,659,976 B2 | 12/2003 | Beck et al. | |
| 6,679,862 B2 | 1/2004 | Diaz et al. | |
| 6,702,779 B2 | 3/2004 | Connelly et al. | |
| 6,750,468 B2 | 6/2004 | Malmstrom et al. | |
| 6,852,094 B2 | 2/2005 | Beck et al. | |
| 6,889,556 B2 | 5/2005 | Steger | |
| 6,907,788 B2 | 6/2005 | Malmstrom et al. | |
| 6,908,452 B2 | 6/2005 | Diaz et al. | |
| 6,979,311 B2 | 12/2005 | Miles et al. | |
| 7,048,715 B2 | 5/2006 | Diaz et al. | |
| 7,059,840 B2 | 6/2006 | Corwin et al. | |
| 7,070,575 B2 | 7/2006 | Beck et al. | |
| 7,092,796 B2 | 8/2006 | Vanderveen | |
| 7,121,143 B2 | 10/2006 | Malmstrom et al. | |
| 7,163,381 B1 | 1/2007 | Barak | |
| 7,356,382 B2 | 4/2008 | Vanderveen | |
| 7,384,408 B2 | 6/2008 | Barak | |
| 7,497,842 B2 | 3/2009 | Diaz et al. | |
| 7,695,448 B2 | 4/2010 | Cassidy et al. | |
| 7,726,174 B2 | 6/2010 | Riley et al. | |
| 7,758,551 B2 | 7/2010 | Wiesner et al. | |
| 7,819,838 B2 | 10/2010 | Ziegler et al. | |
| 7,875,004 B2 | 1/2011 | Yodfat et al. | |
| 7,881,883 B2 | 2/2011 | Remde | |
| 7,892,199 B2 | 2/2011 | Mhatre et al. | |
| 7,896,197 B2 | 3/2011 | Furey et al. | |
| 7,921,718 B2 | 4/2011 | Malmstrom et al. | |
| 7,922,700 B2 | 4/2011 | Evans et al. | |
| 7,967,773 B2 | 6/2011 | Amborn et al. | |
| 7,981,082 B2 | 7/2011 | Wang et al. | |
| 8,025,654 B2 | 9/2011 | Barak | |
| 8,034,020 B2 | 10/2011 | Dewey | |
| 8,048,022 B2 | 11/2011 | Moy et al. | |
| 8,081,069 B2 | 12/2011 | Haueter et al. | |
| 8,105,269 B2 | 1/2012 | Zhou | |
| 8,142,400 B2 | 3/2012 | Rotem et al. | |
| 8,152,780 B2 | 4/2012 | Evans et al. | |
| 8,167,832 B2 | 5/2012 | Bowman et al. | |
| 8,182,461 B2 | 5/2012 | Pope et al. | |
| 8,225,639 B2 | 7/2012 | Riley et al. | |
| 8,232,484 B2 | 7/2012 | Hauck | |
| 8,286,505 B2 | 10/2012 | Wade | |
| 8,287,495 B2 | 10/2012 | Michaud et al. | |
| 8,298,184 B2 | 10/2012 | Diperna et al. | |
| 8,328,786 B2 | 12/2012 | Strickler et al. | |
| 8,343,111 B2 | 1/2013 | Beck et al. | |
| 8,361,021 B2 | 1/2013 | Wang et al. | |
| 8,378,837 B2 | 2/2013 | Wang et al. | |
| 8,394,051 B2 | 3/2013 | Geipel | |
| 8,419,676 B2 | 4/2013 | Evans et al. | |
| 8,448,523 B2 | 5/2013 | Richter | |
| 8,486,005 B2 | 7/2013 | Yodfat et al. | |
| 8,486,020 B2 | 7/2013 | Hills et al. | |
| 8,496,613 B2 | 7/2013 | Zhou | |
| 8,539,672 B2 | 9/2013 | Eggers et al. | |
| 8,567,235 B2 | 10/2013 | Bojan et al. | |
| 8,641,671 B2 | 2/2014 | Michaud et al. | |
| 8,657,778 B2 | 2/2014 | Ziegler et al. | |
| 8,690,014 B2 | 4/2014 | Haueter et al. | |
| 8,690,860 B2 | 4/2014 | Abal | |
| 8,733,178 B2 | 5/2014 | Bivans et al. | |
| 8,752,436 B2 | 6/2014 | Beck et al. | |
| 8,758,323 B2 | 6/2014 | Michaud et al. | |
| 8,771,227 B2 | 7/2014 | Connelly et al. | |
| 8,795,225 B2 | 8/2014 | Lewis et al. | |
| 8,808,230 B2 | 8/2014 | Rotstein | |
| 8,821,432 B2 | 9/2014 | Unverdorben | |
| 8,852,141 B2 | 10/2014 | Mhatre et al. | |
| 8,859,972 B2 | 10/2014 | Cummings et al. | |
| 8,876,787 B2 | 11/2014 | Beck et al. | |
| 8,900,213 B2 | 12/2014 | Pope et al. | |
| 8,926,561 B2 | 1/2015 | Verhoef et al. | |
| 8,943,894 B2 | 2/2015 | Geipel | |
| 8,945,064 B2 | 2/2015 | Gravesen et al. | |
| 8,961,453 B2 | 2/2015 | Bowman et al. | |
| 8,974,415 B2 | 3/2015 | Robert et al. | |
| 8,986,253 B2 | 3/2015 | Diperna et al. | |
| 9,004,886 B2 | 4/2015 | Beck et al. | |
| 9,005,153 B2 | 4/2015 | Kopperschmidt et al. | |
| 9,017,296 B2 | 4/2015 | Beck et al. | |
| 9,033,923 B2 | 5/2015 | Hartman et al. | |
| 9,101,712 B2 | 8/2015 | Denis et al. | |
| 9,109,966 B2 | 8/2015 | Duits | |
| 9,132,230 B2 | 9/2015 | Blomquist | |
| 9,162,023 B2 | 10/2015 | Barnes et al. | |
| 9,173,998 B2 | 11/2015 | Rosinko et al. | |
| 9,211,377 B2 | 12/2015 | Diperna et al. | |
| 9,227,008 B2 | 1/2016 | Magnenat et al. | |
| 9,234,850 B2 | 1/2016 | Hammond et al. | |
| 9,248,230 B2 | 2/2016 | Geipel et al. | |
| 9,272,087 B2 | 3/2016 | Halbert et al. | |
| 9,285,324 B2 | 3/2016 | Leuenberger Jockel | |
| 9,308,323 B2 | 4/2016 | Adams | |
| 9,375,531 B1 | 6/2016 | Lee et al. | |
| 9,408,968 B2 | 8/2016 | Browne et al. | |
| 9,415,158 B2 | 8/2016 | Miller et al. | |
| 9,427,521 B2 | 8/2016 | Pope et al. | |
| 9,468,713 B2 | 10/2016 | Hoenninger, III et al. | |
| 9,474,854 B2 | 10/2016 | Mhatre et al. | |
| 9,480,793 B2 | 11/2016 | Mhatre et al. | |
| 9,480,794 B2 | 11/2016 | Keith et al. | |
| 9,545,478 B2 | 1/2017 | Abal | |
| 9,561,323 B2 | 2/2017 | Plahey et al. | |
| 9,603,998 B2 | 3/2017 | Geipel et al. | |
| 9,610,404 B2 | 4/2017 | Rotstein | |
| 9,642,777 B2 | 5/2017 | Lewis et al. | |
| 9,662,437 B2 | 5/2017 | Moosai | |
| 9,675,756 B2 | 6/2017 | Kamen et al. | |
| 9,677,555 B2 | 6/2017 | Kamen et al. | |
| 9,682,192 B2 | 6/2017 | Marsh et al. | |
| 9,683,562 B2 | 6/2017 | Davis et al. | |
| 9,717,849 B2 | 8/2017 | Mhatre et al. | |
| 9,757,517 B2 | 9/2017 | Eberhard | |
| 9,770,552 B2 | 9/2017 | Hartman et al. | |

(56) References Cited

U.S. PATENT DOCUMENTS

| | | |
|---|---|---|
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 11,033,681 B2 | 6/2021 | Eitan et al. |
| 2003/0141468 A1 | 7/2003 | Malmstrom et al. |
| 2005/0107923 A1 | 5/2005 | Vanderveen |
| 2005/0214129 A1* | 9/2005 | Greene ............. A61M 5/14224 |
| | | 417/18 |
| 2006/0173412 A1 | 8/2006 | Susi |
| 2006/0173421 A1 | 8/2006 | Weber et al. |
| 2006/0189926 A1 | 8/2006 | Hall et al. |
| 2006/0206054 A1 | 9/2006 | Shekalim |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0240201 A1 | 9/2009 | Rotem et al. |
| 2009/0293588 A1 | 12/2009 | Riley et al. |
| 2010/0106082 A1 | 4/2010 | Zhou |
| 2010/0114001 A1 | 5/2010 | O'Mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1* | 2/2013 | Hungerford ...... A61M 5/14228 |
| | | 607/67 |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0214010 A1 | 7/2014 | Kuo et al. |
| 2014/0228755 A1 | 8/2014 | Darrah et al. |
| 2015/0005699 A1 | 1/2015 | Burbank et al. |
| 2015/0005732 A1 | 1/2015 | Halbert et al. |
| 2015/0238689 A1 | 8/2015 | Shimizu |
| 2015/0292500 A1 | 10/2015 | Girard et al. |
| 2015/0367120 A1 | 12/2015 | Kusters et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |
| 2020/0282138 A1 | 9/2020 | Eitan et al. |
| 2021/0178062 A1 | 6/2021 | Eitan |

FOREIGN PATENT DOCUMENTS

| | | | |
|---|---|---|---|
| EP | 1381843 | 3/2009 | |
| EP | 2040056 | 9/2010 | |
| EP | 2902052 | 8/2015 | |
| EP | 1381889 | 3/2016 | |
| EP | 2570826 | 8/2016 | |
| EP | 3834862 | 6/2021 | |
| FR | 2553151 | 4/1985 | |
| GB | 2150644 | 7/1985 | |
| WO | WO-9421918 A1 * | 9/1994 | ............ F04B 43/082 |
| WO | 02/068018 | 9/2002 | |
| WO | 2009/042061 | 4/2009 | |
| WO | 2009/047721 | 4/2009 | |
| WO | 2010/096449 | 8/2010 | |
| WO | 2012/126744 | 9/2012 | |
| WO | 2012/151077 | 11/2012 | |
| WO | 2013/184646 | 12/2013 | |
| WO | 2015/048093 | 4/2015 | |
| WO | 2017/184777 | 10/2017 | |
| WO | 2018/096534 | 5/2018 | |
| WO | 2019/155453 | 8/2019 | |
| WO | 2020/178824 | 9/2020 | |

OTHER PUBLICATIONS

European Search Report dated Jun. 21, 2019 which issued during the prosecution of European Application No. 16817348.2.

An International Search Report and a Written Opinion both dated Aug. 5, 2018, which issued during the prosecution of Applicant's PCT/IL2018/050409.

An Office Action dated Jun. 22, 2020, which issued during the prosecution of U.S. Appl. No. 15/740,365.

European Search Report dated Jun. 4, 2020, which issued during the prosecution of Applicant's European App No. 20160966.6.

An International Search Report and a Written Opinion both dated Jun. 9, 2020, which issued during the prosecution of Applicant's PCT/IL2020/050246.

European Search Report dated May 12, 2021 which issued during the prosecution of Applicant's European App No. 20212979.7.

An Office Action together with an English summary dated Jun. 23, 2020, which issued during the prosecution of Chinese Patent Application No. 201690050050.8.

European Search Report dated Apr. 22, 2021 which issued during the prosecution of Applicant's European App No. 20208122.0.

U.S. Appl. No. 63/075,341, filed Sep. 8, 2020.

U.S. Appl. No. 62/813,897, filed Mar. 5, 2019.

European Search Report dated Oct. 8, 2021 which issued during the prosecution of Applicant's European App No. 18905766.4.

Notice of Allowance dated Aug. 4, 2021, which issued during the prosecution of U.S. Appl. No. 16/808,652.

An International Preliminary Report on Patentability dated May 28, 2019, which issued during the prosecution of Applicant's PCT/IL2017/051276.

An International Search Report and a Written Opinion both dated Jan. 19, 2018, which issued during the prosecution of Applicant's PCT/IL2017/051276.

An Office Action dated Aug. 12, 2020, which issued during the prosecution of U.S. Appl. No. 15/990,658.

An Office Action dated Mar. 26, 2020, which issued during the prosecution of U.S. Appl. No. 15/990,658.

An Advisory Action dated Jan. 13, 2021, which issued during the prosecution of U.S. Appl. No. 15/990,658.

Notice of Allowance dated Mar. 4, 2021, which issued during the prosecution of U.S. Appl. No. 15/990,658.

Notice of Allowance dated May 12, 2021, which issued during the prosecution of U.S. Appl. No. 15/990,658.

European Search Report dated Feb. 17, 2022 which issued during the prosecution of Applicant's European App No. 21194042.4.

* cited by examiner

INFUSION PUMP WITH TOGGLING CAPABILITY

CROSS-REFERENCE TO RELATED APPLICATIONS

The present application:

(a) claims the priority of U.S. 63/075,341 to Eitan et al., filed Sep. 8, 2020, entitled, "Infusion pump with toggling capability," and (b) is a Continuation-In-Part of PCT/IL2020/050246 to Eitan, filed Mar. 4, 2020, entitled "Infusion pump with valve compensation," which published as WO 2020/178824 and claims the priority of U.S. 62/813,897 to Eitan et al., filed Mar. 5, 2019, entitled, "Infusion pump with valve compensation."

Each of the abovementioned applications is incorporated herein by reference.

FIELD OF THE INVENTION

The present invention relates generally to the field of medical devices for providing fluid to a patient. More specifically, the present invention relates to infusion pumps configured to inhibit unintended bolus liquid flow and/or reverse flow by compensation for the descending and/or ascending of the pump's downstream valve.

BACKGROUND

Pumps are often used in the medical industry for delivering fluids, e.g., drugs, or diagnostic fluids, to subjects. One type of medical pump is an infusion pump, used to infuse a fluid into a subject's circulatory system via infusion tubing or a cassette at high accuracy and often for a prolonged period of time. Some infusion pumps pump fluid through the infusion tubing by repeatedly pressing, i.e., squeezing, the tubing.

Occlusions downstream of the pump may occur during the operation of the pump, for example, as a result of a kink in the infusion tube, clamping of the infusion tube, or blood clots. In the event of an occlusion, pressure may build up within the infusion tubing upstream of the occlusion location.

Some known methods for reducing this built-up pressure within an infusion tube are to disconnect the infusion tube from the patient and spill some of the infusion fluid out to release the pressure, which results in a loss of some of the infusion fluid, or to run the pump backwards, which may result in an intake of blood from the patient into the infusion tube.

SUMMARY OF THE INVENTION

A problem of infusion pumps, addressed by some applications of the present invention, is an unwanted suction of a patient's blood as a result of an ascending of the pump's downstream valve and/or an undesired bolus being provided to the patient as a result of a descending of the pump's downstream valve.

In accordance with some applications of the present invention, the herein disclosed infusion pump advantageously includes a controller configured to control the descending/ascending of the plunger along with the ascending/descending of the pump's distal (e.g., downstream) valve, such that the flow caused by the ascending/descending of the pump's distal valve is compensated for by the plunger.

According to some embodiments, before or with opening the distal valve (also referred to herein as the downstream valve), the plunger is lowered, such that a volume of liquid, equal to the volume of blood that would otherwise be sucked into the infusion tube as a result of the ascending of the distal valve, is pumped towards the patient's open vein, thus counteracting/compensating for the unwanted backflow of blood.

Advantageously, such concurrent compensational movement of the plunger vis-à-vis the distal valve ensures that the flow rate of liquid into the patient is essentially devoid of spikes.

According to some embodiments, the valve may ascend and descend at a velocity that is correlated with a set flow rate. This may advantageously ensure that the volume pushed towards the patient by the descent of the downstream valve as well as the volume sucked by the ascent of the downstream valve do not momentarily alter the flow rate.

According to some embodiments, the upper position of the downstream/distal valve may be set such that while in its upper position the distal valve still squeezes the infusion tube in order to reduce boluses caused by the descending of the downstream valve. Advantageously, the distal valve still squeezing the infusion tube while in its upper position also minimizes power consumption, and thus cost of use. Additionally, the distal valve still squeezing the infusion tube while in its upper position ensures that the delivery of the infusion fluid is at an essentially constant volume regardless of a potential degradation of the infusion tube as well as inhibiting or at least reducing tube degradation.

A further undesired effect that is addressed by some applications of the present invention is an unwanted bolus delivery of fluid to the patient after resolution of an occlusion downstream of the pump. Fluid flow to the patient stops in the event of an occlusion downstream of the pump. However, the pump generally continues to pump the fluid toward the patient, resulting in an increase in pressure within the fluid line upstream of the occlusion. The occlusion is detected once a threshold level of pressure is detected, at which point an occlusion alert is triggered and the pump typically stops. The occlusion is typically resolved, e.g., released, by the patient or a clinician. Were the built-up pressure not to be released prior to the occlusion being released, then upon resolution of the occlusion, the volume of the accumulated fluid between the pump and the occlusion site might be delivered to the patient in a short time, i.e., as an unintended bolus. For example, at a delivery flow rate of 1 mL/hr it may take up to 20 min (1200 sec) to reach the occlusion pressure threshold, e.g., 1.2 Bar. After release of the occlusion, it takes around two seconds for the bolus to reach the patient, i.e., the accumulated volume of fluid is delivered to the patient at a flow rate that is 600 times faster than the desired delivery flow rate.

Typically, the volume of the bolus would be smaller than the dose of fluid the patient would have otherwise received by the point in time at which the occlusion is resolved. This is due to the following two factors: (i) during the time it takes the pump to detect the occlusion (while the pump continues to run and the pressure is building up) and for the occlusion to then be resolved, the patient would have otherwise been receiving the fluid, and (ii) fluid flow into the infusion tube from the reservoir slows down as a result of backpressure caused by the occlusion. However, despite the volume of the fluid delivered in the bolus being smaller than what the patient was supposed to receive by that point in time, the flow rate at which the bolus would be delivered to the patient, were the built-up pressure not to be released, is significantly higher than the desired delivery flow rate.

Therefore, in accordance with some applications of the present invention, methods and apparatus are provided for toggling the upstream and downstream valves of a pump upon detection of an occlusion, in order to reduce the pressure built up in the infusion line due to the occlusion. An occlusion downstream of the downstream valve is detected by measuring pressure within the infusion tubing of the pump using a pressure sensor. Once an occlusion is detected, releasing the built-up pressure by toggling the valves typically is performed as follows:
- while the upstream valve remains closed, isolating a segment of the infusion tube between the upstream and downstream valves by closing the downstream valve,
- subsequently, while the downstream valve remains closed, reducing pressure in the isolated segment of the infusion tube by opening the upstream valve,
- subsequently, while the downstream valve remains closed, closing the upstream valve, and
- subsequently, while the upstream valve remains closed, reducing pressure downstream of the downstream valve, i.e., between the downstream valve and the occlusion, by opening the downstream valve.

Typically, the toggling is repeated a plurality of times until the pressure is released, at which point the pump alerts the user or clinician that there is an occlusion. The release of pressure by toggling the valves mitigates the delivery of a bolus of fluid when the occlusion is resolved.

There is therefore provided, in accordance with some applications of the present invention, an infusion pump including:
- a plunger configured to squeeze a section of an infusion tube;
- a proximal valve located proximally to said plunger, said proximal valve configured to:
  - ascend and thereby allow infusion fluid intake from a reservoir to the infusion tube, and
  - descend and thereby inhibit infusion fluid intake from the reservoir to the infusion tube;
- a distal valve located distally to said plunger, said distal valve configured to:
  - ascend and thereby allow infusion fluid flow past the distal valve, and
  - descend and thereby inhibit infusion fluid flow past the distal valve; and
- a controller configured to control said plunger, said proximal valve, and said distal valve and thereby, to control infusion fluid intake from the reservoir and infusion fluid delivery to a subject,
  - wherein controlling delivery of infusion fluid to the subject includes initiating descending of said plunger concurrently with or prior to the ascending of said distal valve, such that the descending of said plunger compensates for suction produced by the ascending of said distal valve, thereby reducing backflow of fluid from the subject.

For some applications, a rate selected from the group consisting of: a rate of the ascending of the distal valve, and a rate of the descending of the distal valve, depends on a set flow rate of the infusion fluid.

For some applications, a rate of descending of the distal valve is determined based on a set flow rate and volume delivered as a result of the descending of the distal valve, wherein the volume delivered as a result of the descending of the distal valve is accounted for as a part of a total infusion fluid volume to be delivered.

For some applications, a motion of the plunger selected from the group consisting of: descending of the plunger, and ascending of the plunger, is continuous.

For some applications, a motion of the plunger selected from the group consisting of: descending of the plunger, and ascending of the plunger, is pulsatory.

For some applications, a motion selected from the group consisting of: the descending of the proximal valve, the ascending of the proximal valve, the descending of the distal valve, and the ascending of the distal valve, is continuous.

For some applications, a motion selected from the group consisting of: the descending of the proximal valve, the ascending of the proximal valve, the descending of the distal valve, and the ascending of the distal valve, is pulsatory.

For some applications, a rate selected from the group consisting of: a rate of ascending of the plunger, and a rate of descending of the plunger, depends on the set flow rate of the infusion fluid.

For some applications, a force sensor configured to measure the pressure in the part of the infusion tube extends between the proximal valve and the distal valve, and wherein the controller is configured to set a rate of the descending of the plunger based on the pressure measured by the force sensor.

For some applications, the distal valve is configured to ascend from a lower position to an upper position, wherein at both the upper position and the lower position, said distal valve is configured to squeeze a section of the infusion tube.

For some applications, the plunger is configured to descend from an upper position to a lower position, wherein at both the upper position and the lower position, said plunger is configured to squeeze a section of the infusion tube.

For some applications, a component of the infusion pump selected from the group consisting of: said plunger and said distal valve, is configured to contact an outer surface of the infusion tube from completion of intake to completion of delivery.

For some applications, the apparatus further includes a motor in communication with said controller, said motor configured to operate said plunger.

For some applications, said motor is further configured to operate at least one valve selected from the group consisting of: said proximal valve, and said distal valve.

For some applications, the apparatus further includes a second motor configured to operate at least one valve selected from the group consisting of: said proximal valve, and said distal valve.

For some applications, infusion tube is a DEHP-free PVC infusion tube, DEHP containing infusion tube, a polyethylene (PE) tube, a silicone tube, a thermoplastic elastomer (TPE) tube, a polypropylene (PP) tube, or a polyurethane tube.

There is further provided, in accordance with some applications of the present invention, an infusion pump including:
- a plunger configured to squeeze a section of an infusion tube;
- a proximal valve located proximally to said plunger, said proximal valve configured to ascend and to descend and thereby allowing and disabling, respectively, infusion fluid intake from a reservoir to the infusion tube;
- a distal valve located distally to said plunger, said distal valve configured to:
  - ascend and thereby allow infusion fluid flow past the distal valve, and descend and thereby inhibit infusion fluid flow past the distal valve; and a controller configured to control said plunger, said proximal valve and said distal valve and thereby to control infusion fluid delivery to a subject and infusion fluid intake from an infusion source, wherein the distal valve is configured to ascend from a lower position to a maximum upper position, wherein at both the maximum upper position and the lower position, said distal valve is configured to squeeze a section of an infusion tube.

For some applications, the ascending of the distal valve from the lower position to the upper position is an ascending from a complete tube occlusion position to a position where greater than 30%, but less than complete occlusion, of the area of the inner tube cross section of the infusion tube is squeezed.

For some applications, the ascending of the distal valve from the lower position to the upper position is performed at a predetermined rate.

For some applications, the ascending of the distal valve from a lower position to an upper position is an ascending from a position where less than 30% of the area of the inner tube cross section of the infusion tube is open to a position where 30%-98% of the area of the inner tube cross section is open.

For some applications, the ascending of the distal valve is performed concurrently with the descending of the plunger.

For some applications, a rate of the ascending of the distal valve depends on a set flow rate of the infusion fluid.

For some applications, a component of the infusion pump selected from the group consisting of: said plunger and said distal valve, is configured to contact an outer surface of the infusion tube from completion of intake to completion of delivery.

There is further provided, in accordance with some applications of the present invention, an infusion pump including:

a plunger configured to squeeze a section of an infusion tube;

a proximal valve located proximally to said plunger, said proximal valve configured to ascend and to descend and thereby allowing and disabling, respectively, infusion fluid intake from a reservoir to the infusion tube;

a distal valve located distally to said plunger, said distal valve configured to:
  ascend and thereby allow infusion fluid flow past the distal valve, and
  descend and thereby inhibit infusion fluid flow past the distal valve thereof;

a force sensor configured to measure the pressure in the part of the infusion tube extending between the proximal valve and the distal valve; and a controller configured to control said plunger, said proximal valve and said distal valve and thereby to control infusion fluid delivery to a subject and infusion fluid intake from an infusion source, wherein controlling delivery of infusion fluid to the subject comprises:
  initiating descending of said plunger prior to or concurrently with an initial, partial ascending of said distal valve, wherein the initial partial ascending of the distal valve is independent of the set flow rate; and
  initiating a continued ascending of the distal valve, wherein a rate of the continued ascending of the distal valve depends on a set flow rate set for the delivery of the infusion fluid and the pressure measured by the force sensor, such that an essentially constant delivery of infusion fluid is obtained.

For some applications, a component of the infusion pump selected from the group consisting of: said plunger and said distal valve, is configured to contact an outer surface of the infusion tube from completion of intake to completion of delivery.

For some applications, the descending of said plunger prior to an initial partial ascending of the distal valve is conducted at a predetermined rate.

For some applications, the descending of said plunger is conducted at a predetermined rate until a reduction of pressure in the infusion tube is detected upon ascending of the distal valve and opening of the infusion tube.

For some applications, the controller is configured to cause said plunger to descend concurrently with the continued ascending of the distal valve.

For some applications, a rate of the descending of the plunger is determined based on the pressure measured by the force sensor.

For some applications, a rate of the descending of the plunger is determined by the set flow rate for the delivery.

There is further provided, in accordance with some applications of the present invention, a method for use with an infusion pump coupled to a fluid reservoir, the infusion pump including an infusion tube, an upstream valve, a downstream valve, a pressing surface disposed between the upstream and downstream valves and configured to press on the infusion tube, and a pressure sensor, the method including:

measuring pressure within the infusion tube using the pressure sensor;

in response to the measured pressure, determining that there is an occlusion in the infusion tube downstream of the downstream valve; and in response to the determination that there is an occlusion, toggling the upstream valve and the downstream valve, the toggling including:
  (a) while the upstream valve remains closed, isolating a segment of the infusion tube between the upstream and downstream valves by closing the downstream valve;
  (b) subsequently, while the downstream valve remains closed, reducing pressure in the isolated segment of the infusion tube by opening the upstream valve;
  (c) subsequently, while the downstream valve remains closed, closing the upstream valve; and
  (d) subsequently, while the upstream valve remains closed, reducing pressure downstream of the downstream valve by opening the downstream valve.

For some applications, toggling includes toggling while the infusion tube is partially squeezed by the pressing surface.

For some applications, the pressure sensor is positioned between the upstream valve and the downstream valve.

For some applications, the method further includes:
  withholding generating an alert indicative of the occlusion in response to determining that there is an occlusion in the infusion tubing; and
  subsequently to the toggling, generating an alert indicating to a user of the infusion pump that there is an occlusion in the infusion tube.

For some applications, the method further includes repeating the toggling a plurality of times, thereby reducing pressure that is in the infusion tube due to the occlusion.

For some applications, the method further includes stopping the toggling after a predetermined number of toggling cycles.

For some applications, the method further includes setting the predetermined number of toggling cycles based on the measured pressure indicative of the occlusion.

For some applications, the method further includes stopping the toggling after a predetermined amount of time.

For some applications, the method further includes setting the predetermined amount of time based on the measured pressure indicative of the occlusion.

For some applications, the method further includes generating an alert indicating to a user of the infusion pump that there is an occlusion in the infusion tube, and repeating the toggling a plurality of times includes repeating the toggling a plurality of times prior to generating the alert.

For some applications, repeating the toggling a plurality of times includes repeating the toggling at least two times prior to generating the alert.

For some applications, repeating the toggling a plurality of times includes repeating the toggling at least five times prior to generating the alert.

For some applications, repeating the toggling a plurality of times includes repeating the toggling up to 100 times prior to generating the alert.

For some applications, repeating the toggling a plurality of times includes repeating the toggling up to 50 times prior to generating the alert.

For some applications, repeating the toggling a plurality of times includes repeating the toggling up to ten times prior to generating the alert.

For some applications, toggling further includes:
repeatedly measuring pressure in the infusion tube; and
regulating the toggling in response to the repeated measuring of the pressure.

For some applications, the method further includes stopping the toggling when at least a threshold pressure decrease, due to the toggling, is detected by the repeated measuring of the pressure.

For some applications, the method further includes stopping the toggling when a pressure value detected during the repeated measuring of the pressure passes below a threshold.

For some applications, the method further includes setting the threshold based on the measured pressure indicative of the occlusion.

For some applications, the method further includes, subsequently to the stopping of the toggling when the pressure value passes below the threshold:
assessing that the infusion tube is no longer occluded in response to detecting a further reduction in pressure in the infusion tube.

For some applications, stopping the toggling includes stopping the toggling based on an amount of time of the toggling, even if the pressure value detected during the repeated measuring of the pressure does not pass below the threshold.

For some applications, stopping the toggling includes stopping the toggling based on a number of toggling cycles, even if the pressure value detected during the repeated measuring of the pressure does not pass below the threshold.

For some applications, stopping the toggling includes stopping the toggling after fewer than 100 toggling cycles, even if the pressure value detected during the repeated measuring of the pressure does not pass below the threshold.

For some applications, stopping the toggling includes stopping the toggling after fewer than 50 toggling cycles, even if the pressure value detected during the repeated measuring of the pressure does not pass below the threshold.

There is further provided, in accordance with some applications of the present invention, apparatus for use with an infusion tube and a fluid reservoir, the apparatus including:
an infusion pump configured to be coupled to the infusion tube and the fluid reservoir, the infusion pump including:
an upstream valve;
a downstream valve;
a pressing surface disposed between the upstream and downstream valves and configured to press on the infusion tube when the infusion pump is coupled to the infusion tube;
a pressure sensor configured to measure pressure within the infusion tube; and
a controller configured to:
in response to the measured pressure, determine that there is an occlusion in the infusion tube downstream of the downstream valve, and
in response to the determination that there is an occlusion, toggle the upstream valve and the downstream valve, the toggling including:
(a) while the upstream valve remains closed, isolating a segment of the infusion tube between the upstream and downstream valves by closing the downstream valve;
(b) subsequently, while the downstream valve remains closed, reducing pressure in the isolated segment of the infusion tube by opening the upstream valve;
(c) subsequently, while the downstream valve remains closed, closing the upstream valve; and
(d) subsequently, while the upstream valve remains closed, reducing pressure downstream of the downstream valve by opening the downstream valve.

For some applications, the controller is configured to perform the toggling of the upstream valve and the downstream valve while the infusion tube is partially squeezed by the pressing surface.

For some applications, the pressure sensor is positioned between the upstream valve and the downstream valve.

For some applications, the controller is further configured to:
withhold generating an alert indicative of the occlusion in response to determining that there is an occlusion in the infusion tube; and
subsequently to the toggling, generate an alert indicating to a user of the infusion pump that there is an occlusion in the infusion tube.

For some applications, the controller is configured to repeat the toggling a plurality of times, thereby reducing pressure that is in the infusion tube due to the occlusion.

For some applications, the controller is configured to stop the toggling after a predetermined number of toggling cycles.

For some applications, the controller is further configured to set the predetermined number of toggling cycles based on the measured pressure indicative of the occlusion.

For some applications, the controller is configured to stop the toggling after a predetermined amount of time.

For some applications, the controller is further configured to set the predetermined amount of time based on the measured pressure indicative of the occlusion.

For some applications, the controller is further configured to generate an alert indicating to a user of the infusion pump that there is an occlusion in the infusion tube, and the controller is configured to repeat the toggling a plurality of times prior to generating the alert.

For some applications, the controller is configured to repeat the toggling at least two times prior to generating the alert.

For some applications, the controller is configured to repeat the toggling at least five times prior to generating the alert.

For some applications, the controller is configured to repeat the toggling up to 100 times prior to generating the alert.

For some applications, the controller is configured to repeat the toggling up to 50 times prior to generating the alert.

For some applications, the controller is configured to:
(a) using the pressure sensor, repeatedly measure the pressure in the infusion tube during the toggling, and
(b) regulate the toggling in response to the repeated measuring of the pressure.

For some applications, the controller is configured to stop toggling when at least a threshold pressure decrease, due to the toggling, is detected by the repeated measuring of the pressure.

For some applications, the controller is configured to stop the toggling when a pressure value detected during the repeated measuring of the pressure passes below a threshold.

For some applications, the controller is further configured to set the threshold based on the measured pressure indicative of the occlusion.

For some applications. the controller is further configured to, subsequently to stopping the toggling when the pressure passes below the threshold, assess that the infusion tube is no longer occluded in response to detecting a further reduction in pressure in the infusion tube.

For some applications, the controller is configured to stop the toggling based on an amount of time of the toggling, even if the pressure value detected during the repeated measuring of the pressure does not pass below the threshold.

For some applications, the controller is configured to stop the toggling based on a number of toggling cycles, even if the pressure value detected during the repeated measuring of the pressure does not pass below the threshold.

For some applications, the controller is configured to stop the toggling after fewer than 100 toggling cycles, even if the pressure value detected during the repeated measuring of the pressure does not pass below the threshold.

For some applications, the controller is configured to stop the toggling after fewer than 50 toggling cycles, even if the pressure value detected during the repeated measuring of the pressure does not pass below the threshold.

For some applications, the controller is configured to stop the toggling after fewer than ten toggling cycles, even if the pressure value detected during the repeated measuring of the pressure does not pass below the threshold.

There is further provided, in accordance with some applications of the present invention, a method for use with an infusion pump coupled to a fluid reservoir, the infusion pump including an infusion tube and a plurality of fluid flow regulators, the fluid flow regulators including an upstream valve, a downstream valve, and a pressing surface disposed between the upstream and downstream valves and configured to press on the infusion tube, the method including:
moving a first one of the fluid flow regulators; and
moving a second one of the fluid flow regulators, such that the first and second fluid flow regulators move in a synchronized manner to affect pressure within the infusion tube at least downstream of the downstream valve, to prevent an undesired pressure condition downstream of the downstream valve.

For some applications, the first one of the fluid flow regulators is the upstream valve, the second one of the fluid flow regulators is the downstream valve, and moving the first and second fluid flow regulators includes toggling the upstream valve and the downstream valve.

For some applications:
the first one of the fluid flow regulators is the downstream valve and moving the first fluid flow regulator includes moving the downstream valve by initiating ascending of the downstream valve, and
the second one of the fluid flow regulators is the pressing surface and moving the second fluid flow regulator includes moving the pressing surface by initiating descending of the pressing surface to compensate for suction produced by the ascending of said downstream valve, thereby reducing backflow of fluid downstream of the downstream valve.

There is further provided in accordance with some applications of the present invention, apparatus for use with an infusion tube and a fluid reservoir, the apparatus including:
an infusion pump configured to be coupled to the infusion tube and the fluid reservoir, the infusion pump including a plurality of fluid flow regulators including:
an upstream valve;
a downstream valve; and
a pressing surface disposed between the upstream and downstream valves and configured to press on the infusion tube when the infusion pump is coupled to the infusion tube; and
a controller configured to move at least two of the fluid flow regulators in a synchronized manner to affect pressure within the infusion tube at least downstream of the downstream valve, to prevent an undesired pressure condition downstream of the downstream valve.

For some applications, the at least two of the fluid flow regulators are the upstream valve and the downstream valve, and the controller is configured to move the at least two of the fluid flow regulators by toggling the upstream valve and the downstream valve to reduce pressure downstream of the downstream valve.

For some applications, the at least two of the fluid flow regulators are the downstream valve and the pressing surface, and the controller is configured to move the at least two fluid flow regulators by initiating descending of the pressing surface concurrently with or prior to ascending of the downstream valve, such that the descending of the pressing surface compensates for suction produced by the ascending of the downstream valve, thereby reducing backflow of fluid downstream of the downstream valve.

The present invention will be more fully understood from the following detailed description of applications thereof, taken together with the drawings, in which:

BRIEF DESCRIPTION OF THE DRAWINGS

Examples illustrative of embodiments are described below with reference to the figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Figure 1:
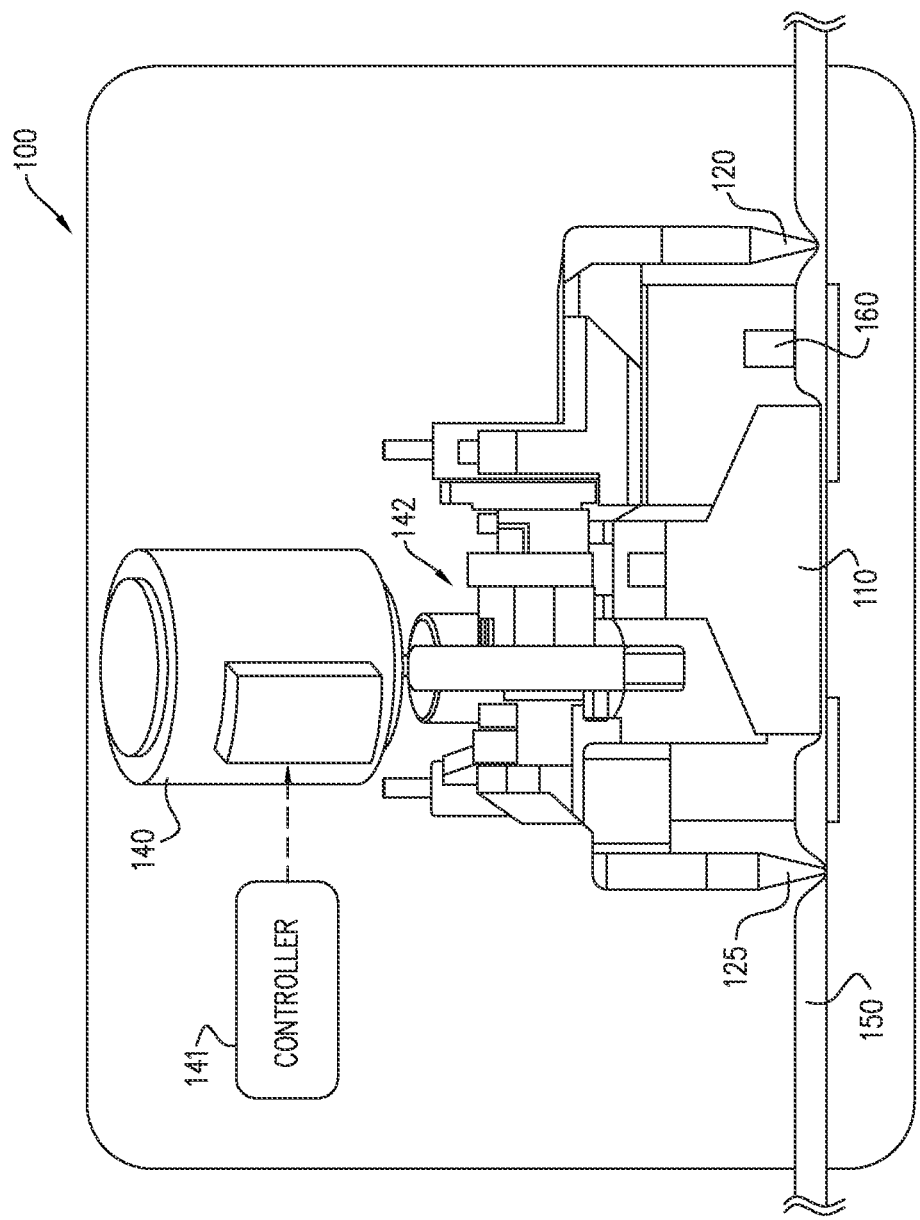
FIG. 1 schematically illustrates an infusion pump, according to some embodiments.

Reference is now made to FIG. 1 which schematically illustrates an infusion pump 100 comprising a plurality of fluid flow regulators. A plunger 110, e.g., a pressing surface such as pressing surface 1030 described hereinbelow, is one of the fluid flow regulators. Another one of the fluid flow regulators is a proximal/upstream valve 120, also referred to herein as an inlet valve, positioned proximally/upstream to plunger 110 and configured to allow flow of infusion fluid from a reservoir (e.g., reservoir 1022 as described hereinbelow with reference to FIGS. 3A-B, 4, and 5A-B) to an infusion tube 150. A third one of the fluid flow regulators is a distal/downstream valve 125, also referred to herein as an outlet valve, positioned distally/downstream to plunger 110 and configured to allow flow of infusion fluid from infusion tube 150 to a patient (not shown). The positioning of plunger 110, proximal valve 120 and distal valve 125 are carried out by motor 140 and associated cam shaft 142, although other embodiments, according to which positioning of plunger 110, proximal valve 120 and distal valve 125 is executed by separate motors, are also possible and within the scope of this disclosure. Motor 140 is typically controlled by a controller 141. Infusion pump 100 further includes a force sensor 160 configured to measure the pressure in the part of infusion tube 150 extending between proximal valve 120 and distal valve 125. The figure illustrates the pump at a state when proximal valve 120 is at a tube releasing position, distal valve 125 is at a tube occluding position and plunger 110 is at a tube squeezing position.

According to some embodiments, there is provided infusion pump 100 comprising the plurality of fluid flow regulators as follows: a plunger configured to squeeze a section of an infusion tube; a proximal valve (also referred to herein as the "upstream valve") located proximally to the plunger; and a distal valve (also referred to herein as the "downstream valve") located distally to the plunger, wherein the distal valve is configured to ascend and thereby allow infusion fluid flow past the distal valve and to descend and thereby inhibit infusion fluid flow past the distal valve; and a controller configured to control the plunger, the proximal valve and the distal valve and thereby to control infusion fluid delivery to a subject and infusion fluid intake from an infusion source.

According to some embodiments, the infusion pump further comprises a pressure sensor. According to some embodiments, the controller is configured to control movement of the plunger based on pressure measurements obtained from the pressure sensor.

According to some embodiments, the controller is configured to move at least two of the fluid flow regulators in a synchronized manner to affect pressure within the infusion tube at least downstream of the downstream valve in order to prevent an undesired pressure condition downstream of the downstream valve. For example, according to some embodiments, the controller is configured to initiate an initial descending of the plunger prior to the ascending of the distal valve so as to create a positive pressure prior to the distal valve opening (while the proximal valve is closed) to compensate immediately for negative (i.e., upstream) fluid flow downstream of the downstream valve that would otherwise result from ascending of the distal valve. According to some embodiments, the controller is configured to initiate a partial initial ascending of the distal valve. According to some embodiments, a partial initial ascending of the distal valve may form a discrete fluid path opening in accordance with a set flow rate requirement. Advantageously such partial initial ascending of the distal valve may better couple the negative (upstream) and positive (downstream) infusion fluid flows and thus reduce boluses. According to some embodiments, the controller is configured to initiate a partial descending of the plunger concurrently with the continued ascending of the distal valve (while the proximal valve is closed). According to some embodiments, this partial descending of the plunger depends on pressure in the section of an infusion tube measured by the pressure sensor. According to some embodiments, the above-described descending of the plunger before or concurrently with the ascending of the distal valve may be referred to herein as a "compensatory" descending of the plunger that compensates for vacuum produced by the ascending of the distal valve, thereby reducing backflow of fluid from the subject. According to some embodiments, the descending of the plunger required for delivering the infusion fluid may be initiated once the distal valve reaches its upper position. As used herein, including in the claims, the term "upper position" of the distal valves refers to the maximum upper position of the distal valve in any given pump cycle, i.e., the upper limit of the distal valve stroke in any given pump cycle. According to some embodiments, the descending of the plunger required for delivering the infusion fluid may be initiated concurrently with the continued ascending of the distal valve to its upper position. According to some embodiments, this distal valve upper position may be dictated by pressure in the section of an infusion tube as measured by the pressure sensor.

According to some embodiments, the compensatory descending of the plunger may be performed separately from the descending of the plunger required for delivering the infusion fluid. According to some embodiments, the compensatory descending rate of the plunger may be same or different than the descending rate of the plunger required for delivering the infusion fluid. According to some embodiments, the compensatory descending of the plunger may be less than the descending of the plunger required for delivering the infusion fluid. According to some embodiments, the compensatory descending of the plunger may be coextensive with (an integral part of) the descending of the plunger required for delivering the infusion fluid.

Typically, the descending of the plunger being either (a) the compensatory descending of the plunger or (b) the descending of the plunger required for delivering the infusion fluid, depends on the state of the distal valve. While the distal valve is occluding the tube, the descending of the plunger is compensatory and acts to increase pressure in the isolated segment of the tube i.e., between the proximal and distal valves, thereby preparing a bolus that compensates for the suction that occurs when the distal valve is opened. For some set flow rates (e.g., less than 300 mL/h), the rate of the compensatory descending of the plunger is typically higher than the rate of the descending of the plunger required for delivering the infusion fluid.

The compensatory descending of the plunger is typically dependent on a predetermined volume of the bolus that compensates for the suction due to the ascending of the distal valve, which relates to parameters of the distal valve, e.g., the geometry of the distal valve, the stroke of the distal valve, and/or the size of the distal valve. Typically, the volume of the bolus prepared during the compensatory descending of the plunger is independent of the "set flow rate" of the infusion fluid (i.e., the flow rate which is set by an operator or programmer of the infusion pump). Contrary to the compensatory descending of the plunger, the descending of the plunger required for delivering the infusion fluid depends on the set flow rate of the infusion fluid.

According to some embodiments, the volume of the prepared bolus during the compensatory descending of the plunger may be calculated and accounted for as a part of the total delivered volume of infusion fluid. According to some embodiments, the compensatory descending of the plunger may be calculated according to pressure in the section of the infusion tube between the proximal and distal valves.

As used herein, the term "compensation" with regards to the plunger refers to a movement of the plunger which counteracts, nullifies, reverses, evens out or otherwise inhibits an undesired flow of infusion fluid to the patient's vein or reverse fluid/blood flow from the patient, caused by movement of the distal valve.

According to some embodiments, the distal valve is configured to ascend from a lower position, at which fluid delivery to the patient is essentially blocked, to an upper position, at which fluid delivery to the patient is facilitated. According to some embodiments, the ascending of the distal valve to the upper position may be minor such that the opening of the tube for delivery remains narrow (e.g. up to 30% area of the inner cross section of the infusion tube). Advantageously, at both the upper position and the lower position, the distal valve at least partially squeezes a section of the infusion tube, thereby reducing the volume of backflow caused by the ascending of the distal valve as well as enhancing the compensation for vacuum produced by the ascending of the distal valve and reducing power consumption. Advantageously, the smaller descending range of the valve reduces the positive flow bolus size.

According to some embodiments, descending of the plunger required for delivering the infusion fluid may be a descending of the plunger from an upper squeezing position to a lower squeezing position, wherein at both the upper squeezing position and the lower squeezing position, the plunger is squeezing a section of an infusion tube, such that an opposite side of an inner surface of the section does not contact the squeezed side, thus ensuring that the delivery of the infusion fluid is at an essentially constant volume regardless of a potential degradation of the infusion tube as well as inhibiting or at least reducing tube degradation.

As used herein, the term "infusion fluid" may refer to any fluid delivered to the patient such as, but not limited to, insulin, nutrients, saline solution, antibiotics, analgesics, anesthetics, hormones, vasoactive drugs, and chelation drugs, and any other therapeutic fluids or combination of fluids.

As used herein, the term "upper squeezing position" with regards to the plunger, refers to a position of a plunger at which an infusion tube is mildly squeezed (i.e., lower than a position at which the tube is not squeezed), without having the opposite sides of an inner surface of the squeezed section contacting one another. According to some embodiments, the delivery phase of the infusion pump is initiated at the "upper squeezing position" or at "after compensation" position. According to some embodiments, the upper squeezing position is higher (less squeezing of the tube) than the position of the plunger when descended to compensate for the backflow caused by the ascending of the distal valve.

As used herein, the term "lower squeezing position" with regards to the plunger, refers to a position of the plunger at which an infusion tube is squeezed to a larger extent as compared to the upper squeezing position, yet still without having the opposite sides of an inner surface of the squeezed section contacting one another.

As used herein, the term "degradation" may refer to the tube losing its springiness, becoming deformed, bottoming out, or otherwise changing its shape or consistency in a manner affecting the drug delivery accuracy. According to some embodiments, the infusion tube may be a DEHP-free PVC infusion tube, a DEHP containing infusion tube, a polyethylene (PE) tube, a silicone tube, a polyurethane tube or the like. Each possibility is a separate embodiment.

According to some embodiments, the velocity of the ascending and descending of the distal valve and/or of the plunger depends on the set flow rate of the infusion fluid. According to some embodiments, the ascending and/or descending of the plunger may be continuous, i.e., at a constant rate. According to some embodiments, the ascending and/or descending of the plunger may be pulsatory, i.e., in small steps. According to some embodiments, the ascending and/or descending of the distal valve may be continuous, i.e., at a constant rate. According to some embodiments, the ascending and/or descending of the distal valve may be pulsatory, i.e., in small steps. That is, at high set flow rates, the velocity of the ascending and descending of the distal valve and/or of the plunger may likewise be high, and at low set flow rates, the velocity of the ascending and descending of the distal valve and/or of the plunger may likewise be low. According to some embodiments, the controller may be configured to automatically adjust the velocity of the ascending and descending of the distal valve and/or of the plunger according to the set flow rate. This ascending/descending sequence and control of movement allow continued fluid delivery flow. For example, the controller may adjust the rate of the descending of the distal valve based on the set flow rate in order to avoid a bolus delivery upon descending of the distal valve, i.e., the rate of the descending of the distal valve is controlled by the controller such that as the distal valve descends the distal valve pushes infusion fluid to the subject at the set flow rate. Thus, for higher flow rates, i.e., faster descending of the plunger, a faster descending of the distal valve may be set, and for lower flow rates, i.e., slower descending of the plunger, a slower descending of the distal valve may be set. The extra volume of fluid pushed to the subject during the descending of the distal valve may be calculated and accounted for as part of the volume of infusion fluid delivered per pump cycle.

Typically, the "upper position" of the distal valve refers to a position of the distal valve at which an infusion tube is squeezed (i.e., lower than a position at which the tube is not squeezed), without having the opposite sides of an inner surface of the squeezed section contacting one another. That is, at the upper position the distal valve engages the infusion tube.

As used herein, the term "lower position" with reference to the distal valve refers to a position of the distal valve at which the infusion tube is squeezed to such extent that delivery of infusion fluid to the patient is essentially avoided.

According to some embodiments, the inner tube cross section of the infusion tube when the distal valve is in its upper position is 30%-98% (e.g., a preset value, e.g., 50%) of the area of the inner tube cross section of the infusion tube, when non-squeezed. Various upper positions for the distal valve may be used, affecting the percentage of the squeezed area, for different set flow rates. For example, while in its upper position the distal valve still squeezes the infusion tube in order to reduce the bolus that is caused by the descending of the distal valve. Nevertheless, while in its upper position the distal valve should be open enough so as not to inhibit delivery of the infusion fluid during the descending of the plunger.

According to some embodiments, for a typical tube of 3 mm inner diameter and a wall thickness of 0.5 mm, a typical upper position, of the distal valve is about 0.3 mm to 2.8 mm, lower than the diameter of a non-squeezed tube. Each possibility is a separate embodiment.

According to some embodiments, the infusion pump is configured to maintain an essentially constant flow rate during the entire delivery of an infusion fluid. As a non-limiting example, the infusion pump is configured to maintain a delivery of an infusion fluid at a set flow rate of 1±0.05 mL/hour for at least 20, at least 36 or at least 96 hours.

According to some embodiments, the pump further includes a motor in communication with the controller, the motor configured to operate the plunger. According to some embodiments, the motor may further be configured to operate the proximal valve, the distal valve or both. Alternatively, the pump may include one or two additional motors configured to operate the proximal valve, the distal valve or both. According to some embodiments, the controller may control the operation of the motor, thereby determining the exact position of the plunger and/or the distal valve. According to some embodiments, the controller may control the operation of the motor, by determining a velocity/rate of the ascending/descending of the plunger, the proximal valve and/or the distal valve. According to some embodiments, the controller may control the operation of the motor, by determining the increments of the ascending/descending of the plunger, the proximal valve and/or the distal valve. According to some embodiments, the controller may control the operation of the motor, by determining the value of the ascending/descending of the plunger, the proximal valve and/or the distal valve.

According to some embodiments, the controller may further be configured to determine a "wait" period, during which the plunger remains at the upper squeezing position, thereby ensuring full engagement of the infusion tube with the plunger, prior to the closing of the infusion pump's upstream valve. This advantageously increases the accuracy of infusion fluid delivery in that the volume delivered remains constant even if the infusion tube has undergone degradation. Furthermore, due to the infusion tube fully engaging the plunger, a persistent ascending of the infusion tube after opening of the upstream valve is essentially inhibited. The length of the wait depends on the flow continuity requirements and the set flow rate. For low set flow rates (0.1-1 mL/hr) and flow continuity of bolus every 20 sec, the wait can last up to 18 sec. For higher set flow rates, the wait time can be shorter (e.g., about 10 sec) and for very high flow rates (999 mL/hr) it may last less than 1 second. The long wait is particularly advantageous for low set flow rates where the tube squeeze duty cycle is very long. The long wait times are essentially a no movement of plunger and valves in the specific position while for high set flow rates the "wait" equals pump's check-in time—the time the pump goes through the encoders that leave the plunger in the upper position while the proximal valve is open.

According to some embodiments, there is provided a method of operation of an infusion pump, the method comprising utilizing the infusion pump, as essentially described herein.

Figure 2A:
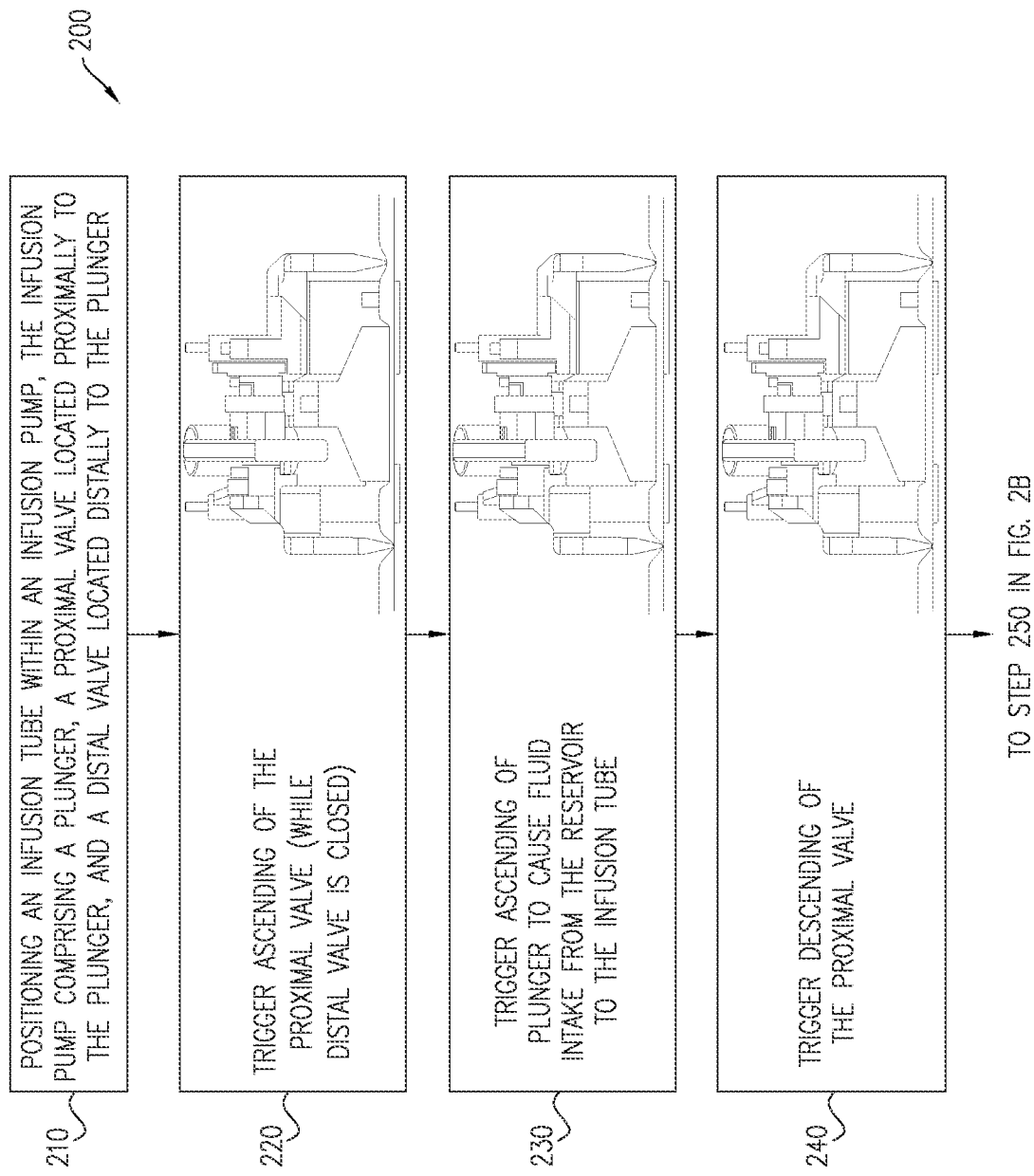
FIGS. 2A-B are, combined, an illustrative flowchart for operating an infusion pump, according to some embodiments.
Figure 2B:
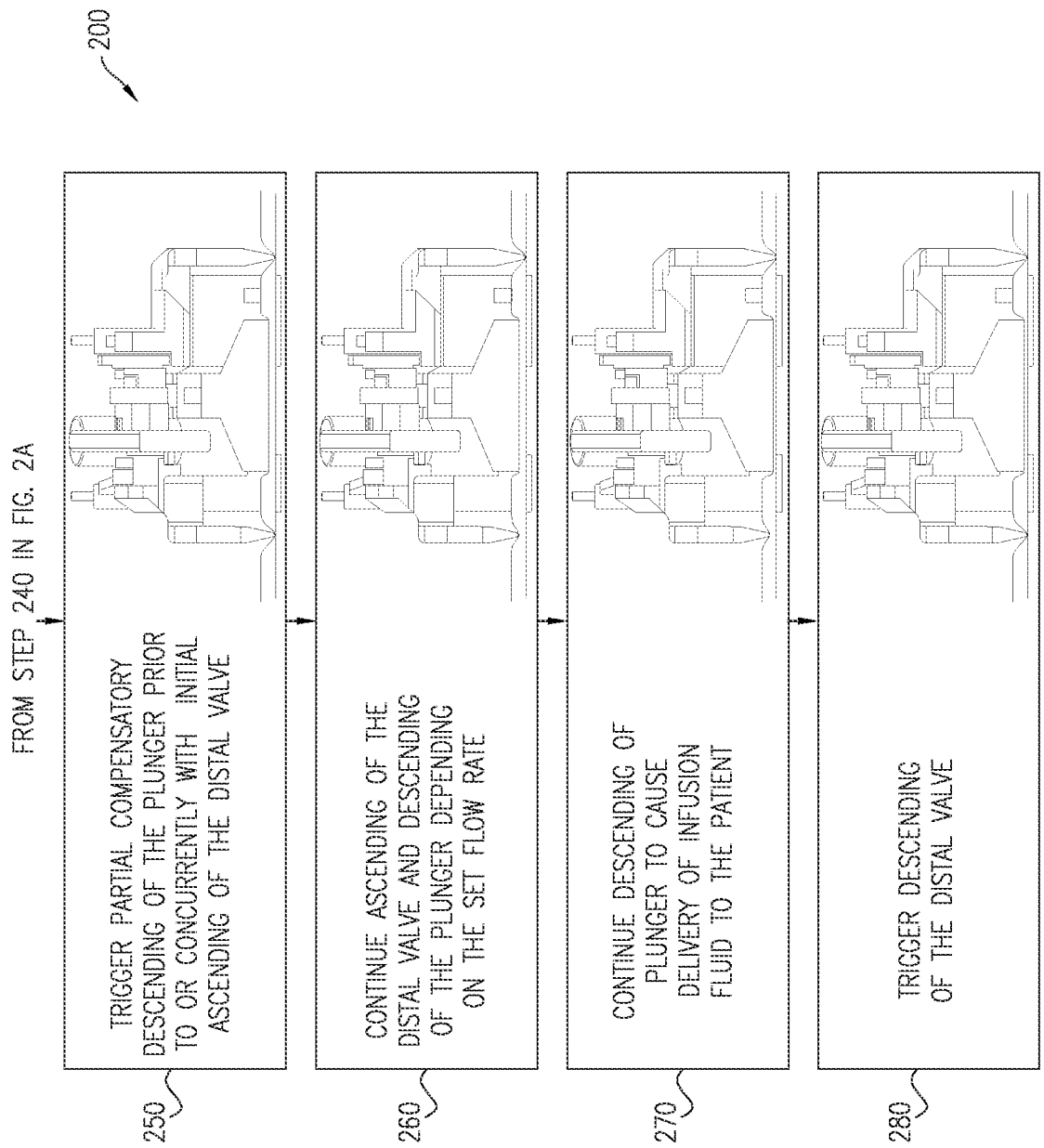

Reference is now made to FIGS. 2A-B which are, combined, an illustrative flowchart 200 for operating an infusion pump, according to some embodiments.

In step 210 an infusion tube is positioned within an infusion pump, the infusion pump comprising a plunger, a proximal valve located proximally to the plunger, and a distal valve located distally to the plunger.

Steps 220 to 240 are steps associated with intake of infusion fluid from a reservoir (also referred to herein as infusion source).

In step 220 an opening of the proximal valve is initiated (while the distal valve is closed), thereby establishing a fluid flow connection between the reservoir and the infusion tube.

In step 230 the plunger is caused to ascend, thereby causing intake of fluid from a reservoir. The ascending of the plunger, causing intake of the infusion fluid from the reservoir, is only initiated once the distal valve has reached its lower position at which the fluid flow connection between the infusion tube and the patient's vein has been closed.

In step 240 descending of the proximal valve is initiated to occlude the fluid line to terminate the fluid intake. The occlusion of the fluid line by proximal valve is completed before the distal valve starts ascending, thereby providing a phase where both valves are closed, during which the compensation step is carried out.

Steps 250 to 280 are steps associated with delivery of the infusion fluid to a patient.

In step 250 a partial, compensatory descending of the plunger is initiated prior to or concurrently with an initial ascending of the distal valve, thereby generating a positive pressure in the tube. Typically, up to 30% of the area of the inner tube cross section of the infusion tube is opened during the initial ascending motion of the distal valve. The compensatory descending of the plunger is configured to ensure that backflow of blood from the patient's vein into the infusion tube, as a result of the ascending of the distal valve, is reduced or inhibited. It is understood that the method alternatively may include two separate steps; a first step (e.g., step 250a) of partial compensatory descending of the plunger prior to the initial ascending of the distal valve and a second step (e.g., step 250*b*) of additional compensatory descending of the plunger concurrently with the ascending of the distal valve. During this step (250 or 250*b*), the pressure in the infusion tube between the valves is measured by the force sensor. If a decrease in pressure is observed, indicating that the distal valve has opened and downstream flow of infusion fluid is facilitated, the plunger transitions to descending at a rate corresponding to the set flow rate of the infusion fluid. It is noted that in the illustrative figure of step 250 the plunger and the distal valve appear to be in the same position as they are in the illustrative figure of step 240. The partial compensatory descending of the plunger is small and therefore not noticeably shown in the figure. Additionally, the distal valve is shown closed, since the partial compensatory descending of the plunger may occur prior to the initial ascending of the distal valve.

In step 260 the ascending of the distal valve and the descending of the plunger is continued. According to some embodiments, the rate of the ascending of the distal valve increases with the set flow rate, e.g., for higher set flow rates the distal valve ascends at a higher rate.

Optionally, in step 270 the plunger is further lowered thereby causing the infusion fluid to be delivered to the patient. Alternatively, the continuous ascending of the distal valve in step 260 may be very slow and prolonged, such that the delivery of the infusion fluid becomes an integral part of step 260.

In step 280, upon the plunger having completed the squeezing of the infusion tube, a descending of the distal valve is initiated to occlude the infusion line. The volume delivered due to descending of the distal valve may be determined and taken into account as part of the total volume of infusion fluid delivered, as described hereinabove. The rate of the descending of the distal valve may be adjusted to match the set flow rate of delivery.

It is understood that upon completion of infusion fluid delivery, additional intake/delivery cycles may be performed by repeating steps 220 through 280.

Figure 3A:
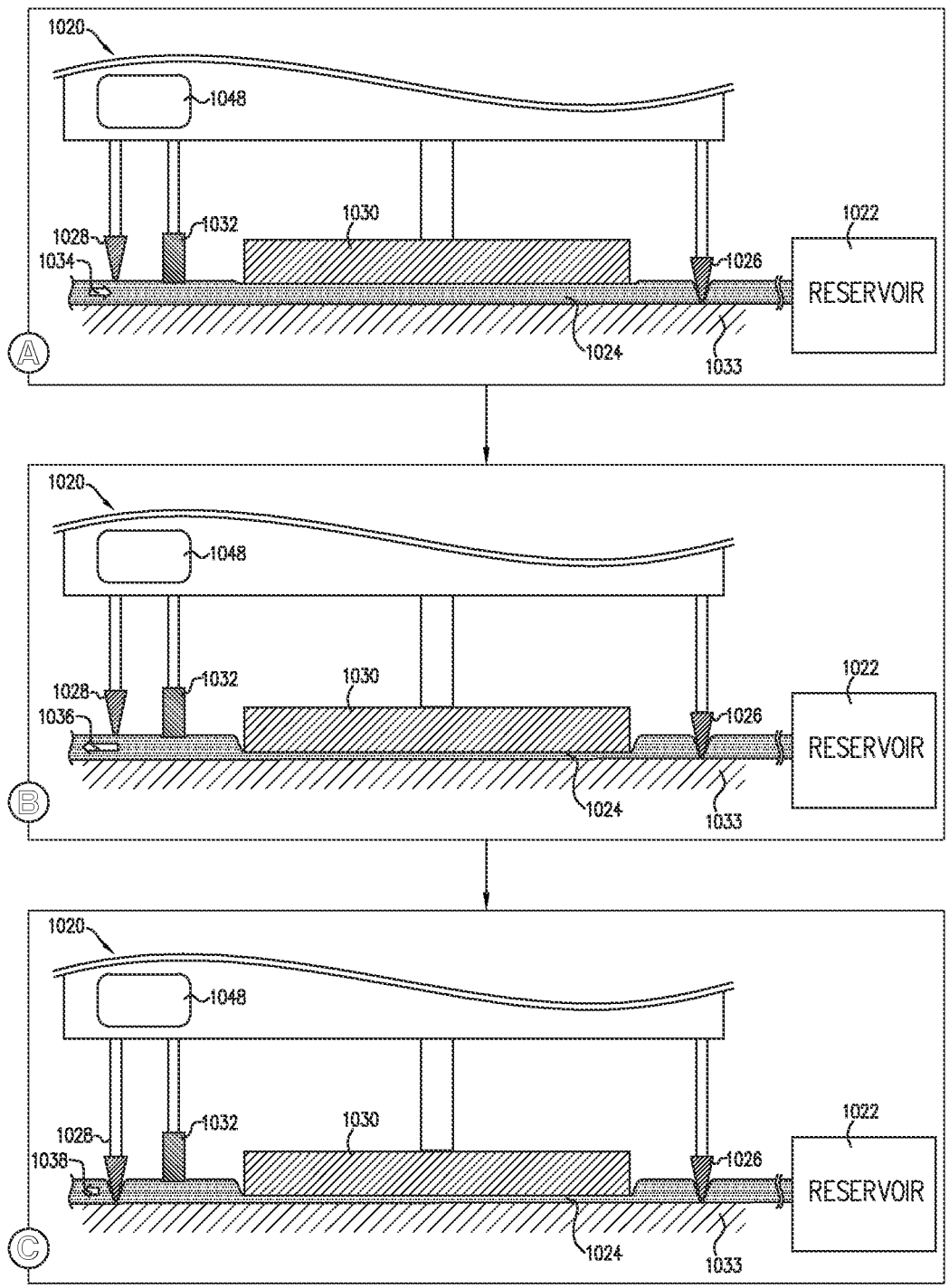
FIGS. 3A-B are, combined, a schematic illustration of the pumping cycle of an infusion pump, according to some applications of the present invention.
Figure 3B:
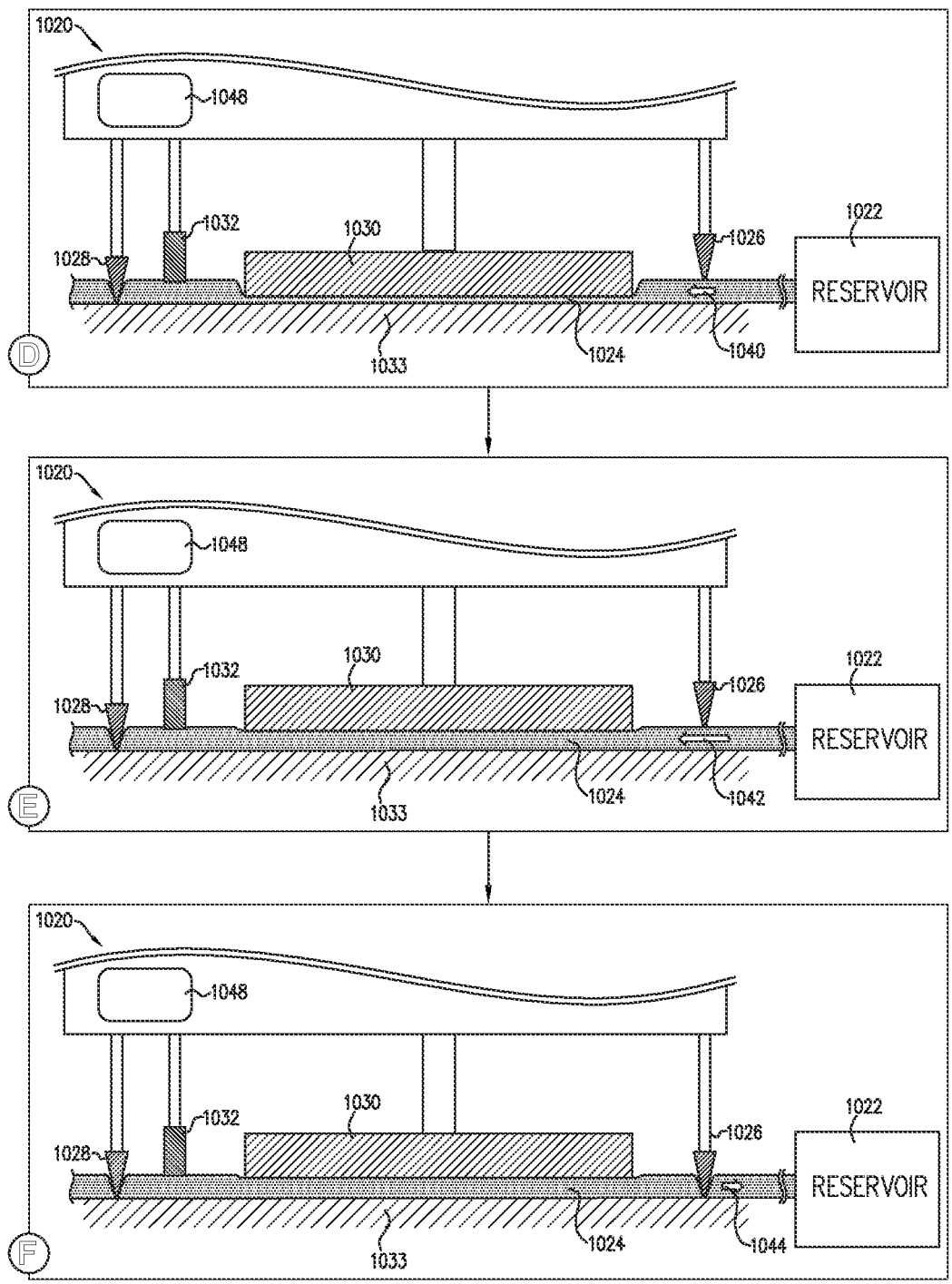

Reference is now made to FIGS. 3A-B, which are illustrations of a pumping cycle of an infusion pump 1020. Infusion pump 1020 is coupled to a fluid reservoir 1022, e.g., an infusion bag or a syringe, and includes (i) an infusion tube 1024, (ii) a plurality of fluid flow regulators including an upstream valve 1026, a downstream valve 1028, and a pressing surface 1030, e.g., a plunger such as plunger 110 described hereinabove with reference to FIG. 1 (which is disposed between upstream valve 1026 and downstream valve 1028 and presses on infusion tube 1024), (iii) a pressure sensor 1032 configured to measure pressure within infusion tube 1024, and (iv) a controller 1048, e.g., a computer processor, further described hereinbelow with reference to FIGS. 4 and 5A-B. According to some embodiments, controller 1048 is configured to move at least two of the fluid flow regulators (e.g., upstream valve 1026 and downstream valve 1028) in a synchronized manner (e.g., by toggling upstream valve 1026 and downstream valve 1028 as further described hereinbelow with reference to FIGS. 5A-B) to affect pressure within the infusion tube at least downstream of the downstream valve in order to prevent an undesired pressure condition (e.g., an undesired bolus delivery due to built-up pressure) downstream of downstream valve 1028.

FIGS. 3A-B depict steps A-F of the regular pumping cycle of infusion pump 1020. It is noted that while the pumping cycle is depicted as starting from the opening of downstream valve 1028 for delivery, this is not limiting and the pumping cycle may begin from any other point within the cycle, e.g., intake of fluid from reservoir 1022. It is also noted that for the sake of clarity of the illustration, each element in FIGS. 3A-B is labeled only one time.

In step A, upstream valve 1026 is closed and downstream valve 1028 is opened for the start of delivery of the infusion fluid to the patient. Arrow 1034 illustrates that as downstream valve 1028 is opened a small amount of backflow may occur due to the opening of the valve. In step B, pressing surface 1030 is lowered in order to squeeze infusion tube 1024 and thereby cause the infusion fluid to flow toward the patient (not shown), as indicated by arrow 1036. In step C, once the delivery of the infusion fluid for that particular pumping cycle is complete, downstream valve 1028 is closed. Arrow 1038 illustrates that as downstream valve 1028 is closed a small amount of infusion fluid moves along infusion tube 1024 toward the patient due to the closing of the valve. For some applications, following step C, both upstream valve 1026 and downstream valve 1028 are maintained closed for a duration of time referred to herein as a "security zone" prior to the opening of upstream valve 1026, i.e., downstream valve 28 is closed prior to upstream valve 1026 being opened so as to prevent free flow of the infusion fluid to the patient upon the opening of upstream valve 1026.

In step D, the intake phase of the pumping cycle begins with the opening of upstream valve 1026 while downstream valve 1028 remains closed. Arrow 1040 illustrates that as upstream valve 1026 is opened a small amount of suction may occur due to the opening of the valve, causing a small amount of flow from reservoir 1022.

In step E, pressing surface 1030 is raised from the position it was lowered to in step B in order to create negative pressure within infusion tube 1024 to draw infusion fluid from reservoir 1022 into infusion tube 1024, as indicated by arrow 1042.

In step F, upstream valve 1026 is closed once the intake of infusion fluid from reservoir 1022 for that pumping cycle is complete. Arrow 1044 illustrates that as upstream valve 1026 is closed, a small amount of backflow may occur toward reservoir 1022 due to the closing of the valve. For some applications, following step F, both upstream valve 1026 and downstream valve 1028 are again maintained closed for a security zone, after which infusion pump 1020 returns to step A with the opening of downstream valve 1028.

Pressure sensor 1032 is positioned so as to measure pressure within infusion tube 1024. For some applications, pressure sensor 1032 may be any sensor configured to measure the pressure within infusion tube 1024, such as, but not limited to, a piezoelectric sensor, a gauge sensor, an optical sensor, a proximity sensor, or any combination thereof. For some applications, pressure sensor 1032 is positioned between upstream valve 1026 and downstream valve 1028.

Figure 4:
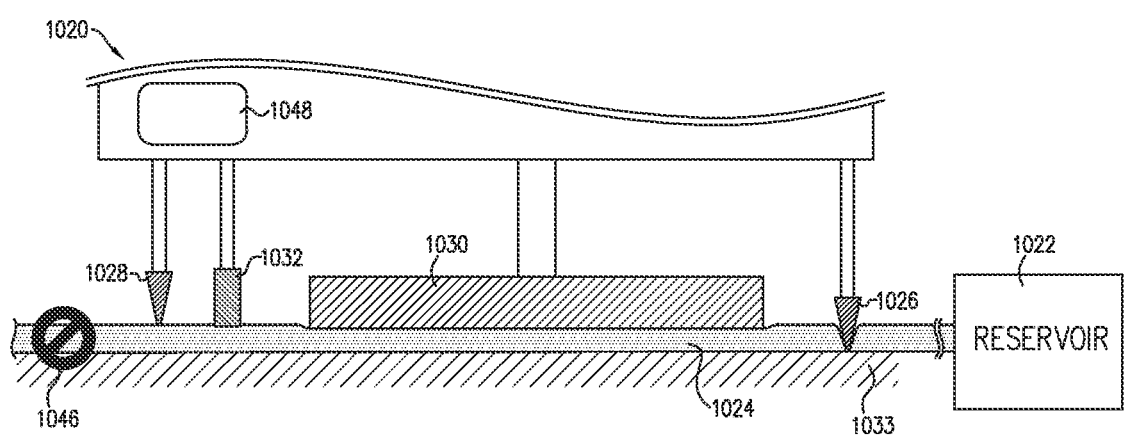
FIG. 4 is a schematic illustration of an occlusion downstream of a downstream valve of the infusion pump, in accordance with some applications of the present invention.

Reference is now made to FIG. 4, which is a schematic illustration of an occlusion 1046 downstream of downstream valve 1028, in accordance with some applications of the present invention. For some applications, a controller 1048, e.g., a computer processor, is configured to, in response to the measured pressure within infusion tube 1024, determine that there is an occlusion 1046 in infusion tube 1024 downstream of the downstream valve 1028. For example, controller 1048 may determine that there is an occlusion 1046 in infusion tube 1024 in response to the measured pressure within infusion tube 1024 reaching an occlusion threshold value.

When occlusion 1046 occurs in infusion tube 1024 downstream of downstream valve 1028, the infusion fluid is prevented or at least inhibited from being delivered to the patient as pump 1020 continues to pump, and as such causes an increase in pressure within infusion tube 1024 between infusion pump 1020 and occlusion 1046. Typically, the pressure continues to increase until an occlusion threshold value is reached indicating that there is an occlusion within infusion tube 1024. As described hereinabove, were occlusion 1046 to be resolved prior to the built-up pressure being released, then the accumulated infusion fluid might be delivered to the patient as a bolus delivery at a flow rate that is typically substantially higher than the desired delivery flow rate, e.g., at least 5 times higher, e.g., at least 10 times higher, e.g., at least 50 times higher than the desired delivery flow rate. Therefore, in accordance with some applications of the present invention, in response to the determination that there is an occlusion 1046, controller 1048 toggles upstream valve 1026 and downstream valve 1028 in order to release the built-up pressure, as described hereinbelow with reference to FIGS. 5A-B.

Figure 5A:
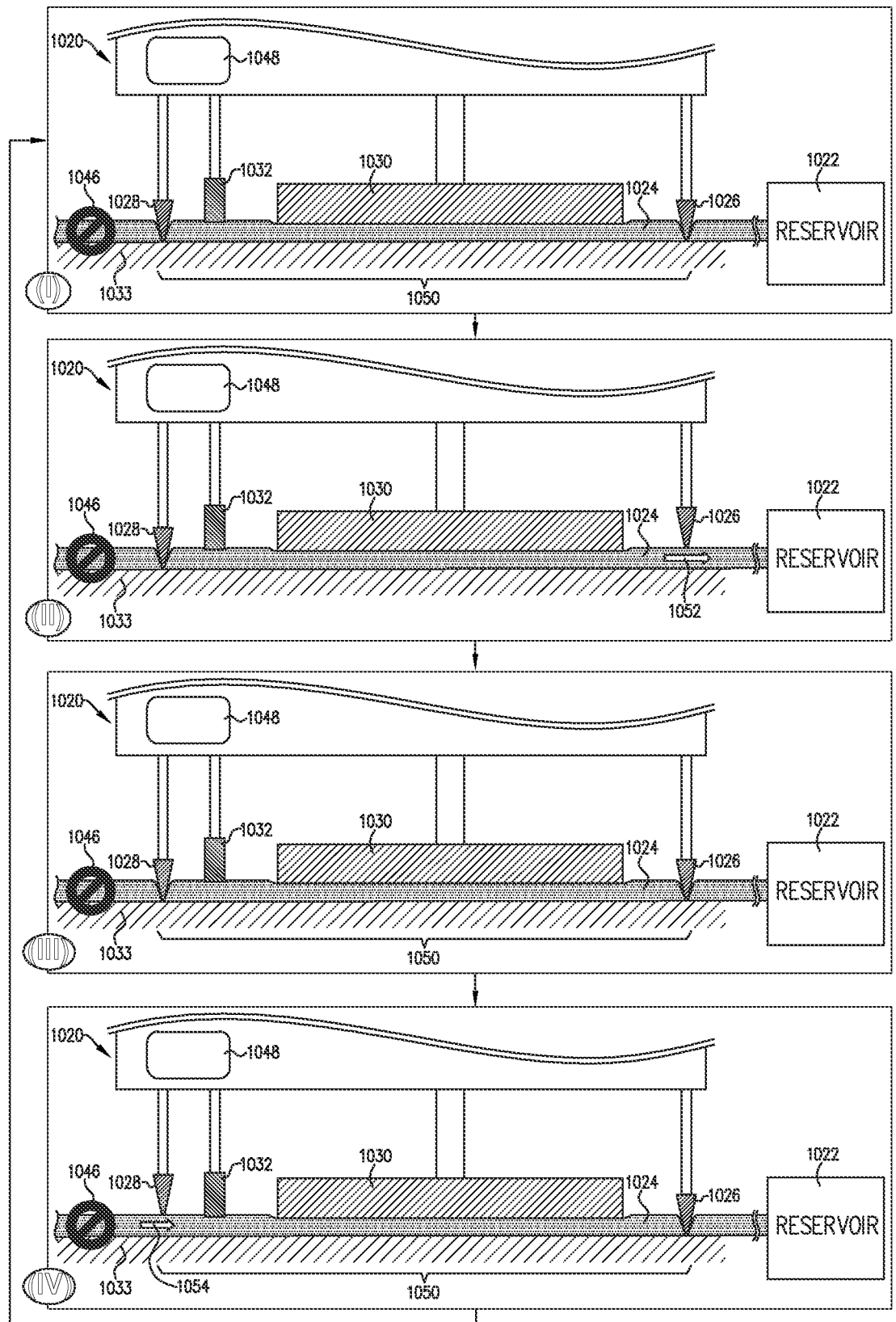
FIG. 5A is an illustrative flow diagram depicting the steps of toggling the upstream and downstream valves of the infusion pump, in accordance with some applications of the present invention.

Reference is now made to FIG. 5A, which is an illustrative flow diagram depicting the steps of the toggling in order to release the built-up pressure in infusion tube 1024 due to the occlusion, in accordance with some applications of the present invention. The steps of the toggling are as follows:

Step (I): while upstream valve 1026 remains closed, isolating a segment 1050 of infusion tube 1024 between upstream valve 1026 and downstream valve 1028 by closing downstream valve 1028, Step (II): subsequently, while downstream valve 1028 remains closed, reducing pressure in isolated segment 1050 of infusion tube 1024 by opening upstream valve 1026 (arrow 1052 illustrates that the pressure is reduced by some infusion fluid flowing back toward reservoir 1022 upon the opening of upstream valve 1026), Step (III): subsequently, while downstream valve 1028 remains closed, closing upstream valve 1026, isolating segment 1050 again, and Step (IV): subsequently, while upstream valve 1026 remains closed, reducing pressure downstream of downstream valve 1028 by opening downstream valve 1028 (arrow 1054 illustrates that the pressure is reduced by some of the infusion fluid flowing upstream from downstream of downstream valve 1028 upon the opening of downstream valve 1028; since some of the pressure was already reduced in step (II), arrow 1054 is depicted as slightly smaller than arrow 1052).

It is noted that an implementation is shown in FIG. 5A in which the toggling is performed while pressing surface 1030 is shown to be in its upper position, yet still slightly squeezing infusion tube 1024. Typically (but not necessarily), pressing surface 1030 is always in contact with infusion tube 24, even in its upper position (as shown in FIGS. 3A-B as well). Typically, the toggling is performed without moving pressing surface 1030, such that the built-up pressure in infusion tube 1024 is passively released due to the toggling of upstream valve 1026 and downstream valve 1028. For some applications, the toggling is performed while pressing surface 1030 is maintained in whatever position it was in when the occlusion was detected, such that the toggling is performed without moving pressing surface 1030. For some applications, pressing surface 1030 is moved to its upper position for the toggling; in this case pressing surface is moved to its upper positioned when downstream valve 1028 is closed and upstream valve 1026 is open so as to avoid backflow of infusion fluid and/or blood from the patient.

It is noted that during the toggling, the opening of upstream valve 1026 is typically only performed while the downstream valve 1028 is closed, and the opening of downstream valve 1028 is typically only performed while upstream valve 1026 is closed. This is to prevent free-flow of the infusion fluid from reservoir 1022 to the patient in the event that the occlusion is released, e.g., accidentally released, during the toggling.

Arrow 1056 indicates that the toggling is iteratively repeated a plurality of times, further described hereinbelow.

Figure 5B:
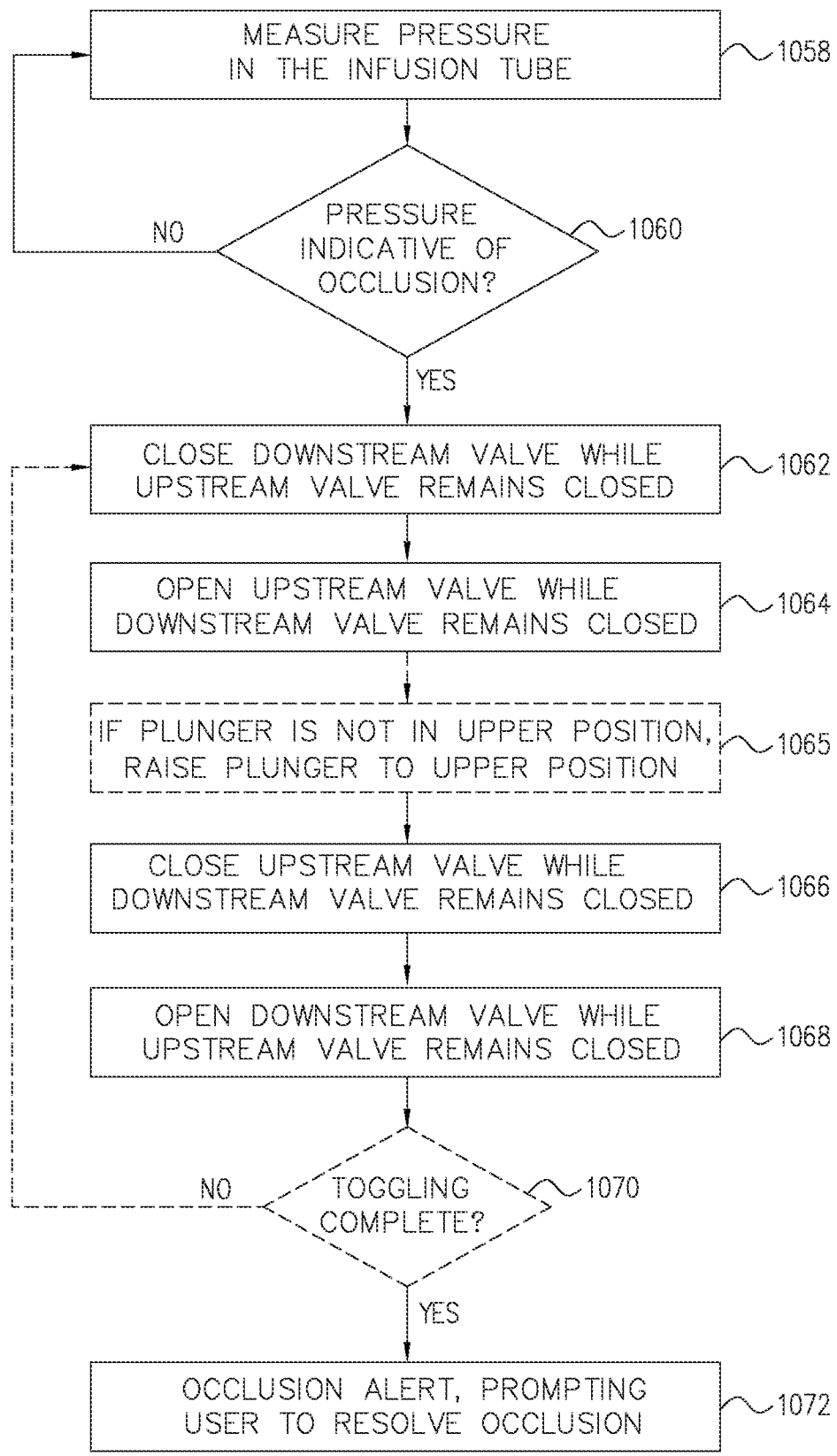
FIG. 5B is a flowchart depicting the process of detecting an occlusion and toggling of the upstream and downstream valves in order to release the built-up pressure due to the occlusion, in accordance with some applications of the present invention.

Reference is now made to FIG. 5B, which is a flowchart depicting the process of detecting an occlusion, e.g., occlusion 1046, in infusion tube 1024 and toggling of upstream valve 1026 and downstream valve 1028 in order to release the built-up pressure due to the occlusion, in accordance with some applications of the present invention. As described hereinabove, pressure is measured within infusion tube 1024 (step 1058) and controller 1048 determines that there is an occlusion downstream of the pump in response to the measured pressure, e.g., in response to the measured pressure reaching an occlusion threshold value. Decision diamond 1060 indicates that (a) if the measured pressure does not indicate an occlusion then pump 1020 continues to run while measuring the pressure within infusion tube 1024, and (b) if the pressure within infusion tube 1024 is indicative of an occlusion then the toggling of upstream valve 1026 and downstream valve 1028 (as described hereinabove with reference to FIG. 5A) is performed in order to release the built-up pressure. Steps (I), (II), (III), and (IV) of the toggling depicted in FIG. 5A correspond respectively to steps 1062, 1064, 1066, and 1068 of FIG. 5B.

For some applications, as indicated by decision diamond 1070, the toggling is iteratively repeated a plurality of times until controller 1048 determines that the toggling is complete. For some applications, controller 1048 stops the toggling, i.e., determines that the toggling is complete, after a predetermined number of toggling cycles, e.g., 10, 50, or 100 toggling cycles. Controller 1048 may set the predetermined number of toggling cycles in response to the measured pressure indicative of the occlusion. Alternatively or additionally, for some applications, the predetermined number of toggling cycles may be set based on (a) a length of infusion tube 1024, (b) a distance between upstream valve 1026 and downstream valve 1028, (c) the specific infusion fluid, e.g., based on a level of risk associated with deviation of the delivery rate for a specific fluid or medication, and/or (d) based on the delivery flow rate of the infusion.

With respect to the length of infusion tube 1024, the inventors have realized that as the length of infusion tube 1024 between occlusion 1046 and pump 1020 increases, it takes a higher number of toggling cycles to release the built-up pressure upstream of the occlusion. Therefore, for a long infusion tube 1024 where occlusion 1046 may be up to 2 m away from pump 1020, controller 1048 may set the predetermined number of toggling cycles to be higher than for a shorter infusion tube 1024.

With respect to the distance between upstream valve 1026 and downstream valve 1028, the inventors have realized that as the length of isolated segment 1050, between upstream valve 1026 and downstream valve 1028, increases, it takes fewer toggling cycles to release the built-up pressure upstream of the occlusion. This is due to a higher amount of pressure being released per toggling cycle (further described with reference to FIG. 6). For example, a pump with a short isolated segment may require twice as many toggling cycles as a pump with an isolated segment that is twice the length.

With respect to the specific infusion fluid, for some applications, controller 1048 may have a setting that changes the pressure thresholds or the predetermined number of toggling cycles, or may entirely disable the toggling based on the specifics of a given clinical application. For example, for a particular drug in a particular clinical application it may be more desirable to give the entire missed volume in a single administration than to have the patient not receive any drug while the pressure is being released by the toggling, whereas for a different particular drug, e.g., a particularly potent drug, in a different particular clinical application, it may be harmful to the patient to give the entire missed volume in a single administration, in which case the toggling cycles are used to reduce the built-up pressure. Therefore, there is a tradeoff between whether an under-delivery or over-delivery is more desirable for a particular drug in the particular clinical application.

With respect to the delivery flow rate, controller 1048 may set the predetermined number of toggling cycles such that when occlusion 1046 is released the flow rate of the bolus delivery to the patient is relatively similar to the delivery flow rate. For example, with a high delivery flow rate, the flow rate of the potential unintended bolus (were the built-up pressure not to be released) may not be particularly different from the high delivery flow rate. In this case, controller 1048 may set the predetermined number of toggling cycles to be low or may disable the toggling feature completely. By contrast, with very low delivery flow rates, the flow rate of the potential unintended bolus (were the built-up pressure not to be released) would cause a high over-delivery rate with respect to the intended low delivery flow rate. This may be undesirable, e.g., for drugs having immediate effect on a patient's heart.

For some applications, controller 1048 stops the toggling, i.e., determines that the toggling is complete, after a predetermined amount of time, e.g., 0.5-15 seconds, e.g., 3 seconds. For some applications, the predetermined amount of time may be based on the measured pressure indicative of the occlusion, e.g., controller 1048 may set the predetermined amount of time in response to the measured pressure indicative of the occlusion. Alternatively or additionally, and as described hereinabove with regard to the predetermined number of toggling cycles, mutatis mutandis, for some applications, the predetermined amount of time may be set based on (a) a length of infusion tube 1024, (b) a distance between upstream valve 1026 and downstream valve 1028, (c) the specific infusion fluid, e.g., based on a level of risk associated with deviation of the delivery rate for a specific fluid or medication, and/or (d) based on the delivery flow rate of the infusion.

For some applications, using pressure sensor 1032, controller 1048 repeatedly measures the pressure in infusion tube 1024 during the toggling, and regulates the toggling in response to the repeated measuring of the pressure. For example, controller 1048 may stop the toggling, i.e., determine that the toggling is complete, when at least a threshold pressure decrease, due to the toggling, is detected by the repeated measuring of the pressure. Alternatively or additionally, controller 1048 may stop the toggling, i.e., determine that the toggling is complete, when a pressure value detected during the repeated measuring of the pressure passes below a threshold. For some applications, controller 1048 may set the threshold based on the measured pressure indicative of the occlusion.

For some applications, even if the pressure value detected during the repeated measuring of the pressure does not pass below the threshold, controller 1048 may stop the toggling based on (a) an amount of time of the toggling or (b) a number of toggling cycles, e.g., after fewer than 100 toggling cycles, e.g., after fewer than 50 toggling cycles, e.g., after fewer than 10 toggling cycles. For example, if after a predetermined amount of time or number of toggling cycles the pressure in infusion tube 1024 has still not decreased, then it may be an indication of something in pump 1020 not working correctly, e.g., pressure sensor 1032 not working, or one or both of upstream valve 1026 and downstream valve 1028 not working. Alternatively, if after a predetermined amount of time or number of toggling cycles the pressure in infusion tube 1024 has still not decreased, it may be due to another device having been connected to the same port on the patient's body and causing a continuous elevated pressure level which controller 1048 of pump 1020 may incorrectly interpret as an occlusion. In this case, continuous upstream flow may be caused if the toggling cycles were to continue indefinitely until a pressure decrease is detected. For some applications, controller 1048 may generate an alert if after a predetermined amount of time or number of toggling cycles the pressure in infusion tube 1024 has still not decreased, e.g., if the pressure remains at or above the threshold.

Step 1072 indicates that an occlusion alert is generated after the toggling is complete. As described hereinabove, toggling the upstream and downstream valves enables the built-up pressure from the occlusion to be released prior to the occlusion being resolved. Therefore, for some applications, even though controller 1048 has determined the presence of an occlusion in infusion tube 1024, an alert is not generated until after the toggling is complete. That is, the toggling is repeated a plurality of times, e.g., at least 2 times, e.g., at least 5 times, e.g., up to 100 times, e.g., up to 50 times, prior to generating the alert. Thus, for some applications, controller 1048 withholds generating an alert indicative of the occlusion until in response to determining that there is an occlusion, and subsequently to the toggling, the controller generates an alert indicating to a user of infusion pump 1020 that there is an occlusion in infusion tube 1024 (step 72). The user may then be prompted to resolve the occlusion.

For some applications, the valves are toggled until the built-up pressure due to the occlusion is largely or entirely released. However, it is possible that if the pressure is released and subsequently the occlusion is not actually resolved, e.g., due to human error, it may be a considerable amount of time before the pressure increases again to the occlusion pressure threshold, resulting in a long time without delivery of the fluid to the patient. Therefore, for some applications, the built-up pressure is reduced only to a point where a hazardous bolus would be avoided, e.g., the pressure threshold indicating that the toggling is complete may be above zero, e.g., 0.3 bar, and the remainder of the pressure is released by opening downstream valve 1028 after the occlusion has been resolved, e.g., after a clinician or user confirms resolution of the occlusion and/or has turned off the occlusion alert. Once resolution of the occlusion has been confirmed, controller 1048 opens downstream valve 1028 measures the pressure. Alternatively, subsequently to pump 1020 resuming delivery after resolution of an occlusion, controller 1048 may set the occlusion pressure level to be very low, e.g., zero bar, such that if the occlusion was not resolved and the pressure begins to increase again, pump 1020 will stop relatively quickly in order to reduce the pressure and alert the user again to the presence of the occlusion.

For some applications, setting the pressure threshold that indicates to controller 1048 that the toggling is complete to an above-zero level, e.g., 2 bar, enables controller 1048 to detect the resolution of the occlusion by detecting a further reduction in pressure in the infusion tube that occurs upon resolution of the occlusion. Thus, for some applications, subsequently to stopping the toggling when the pressure passes below the threshold, controller 1048 assesses that infusion tube 1024 is no longer occluded in response to detecting a further reduction in pressure in infusion tube 1024.

Figure 6:
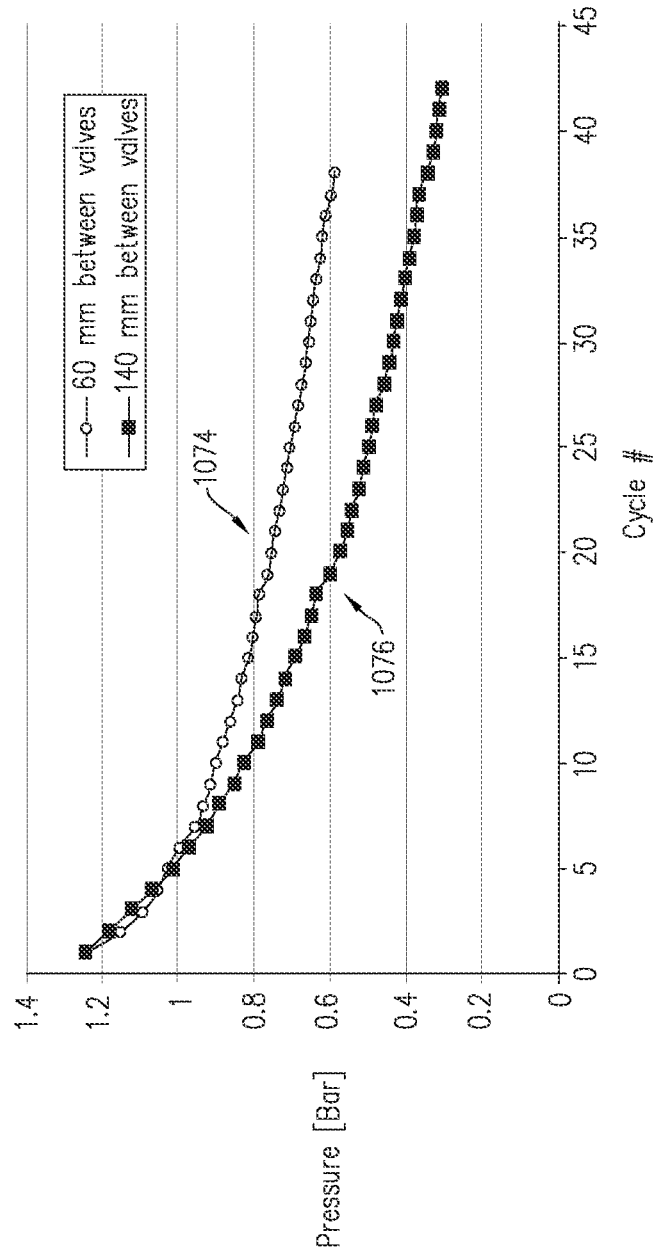
FIG. 6 is a graph showing results from an experiment carried out by the inventors, in accordance with some applications of the present invention.

Reference is now made to FIG. 6, which is a graph showing results from an experiment carried out by the inventors, in accordance with some applications of the present invention. In the experiment an occlusion was artificially created by clamping infusion tube 1024 downstream of downstream valve 1028, creating approximately a 1.2 Bar pressure downstream of downstream valve 1028. An infusion bag was positioned 50 cm above upstream valve 1026 and downstream valve 1028. Toggling of upstream valve 1026 and downstream valve 1028 was performed as described hereinabove with reference to FIGS. 5A-B. The experiment was carried out using two different pump geometries: (1) a Q-Core administration set (AS) (AP-404) with having a segment of 60 mm between upstream valve 1026 and downstream valve 1028 (curve 1074), and (2) a Fresenius AS tube with having a segment of 140 mm between upstream valve 1026 and downstream valve 1028 (curve 1076). FIG. 6 shows the pressure results obtained from the experiment. As seen from the graph, for both infusion tubes, the pressure decreased as a function of the number of toggling cycles. Additionally, as seen, the number of toggling cycles it takes to reduce the pressure to a given pressure level appears to depend on the distance between upstream valve 1026 and downstream valve 1028. When the distance between the valves is larger, the amount of infusion fluid flowing back toward the infusion bag when upstream valve 1026 is opened during the toggling is larger and thus fewer toggling cycles are needed to release the pressure built up in infusion tube 1024 due to the occlusion.

Applications of the invention described herein can take the form of a computer program product accessible from a computer-usable or computer-readable medium (e.g., a non-transitory computer-readable medium) providing program code for use by or in connection with a computer or any instruction execution system, such as controllers 141 and 1048. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., controller 141, and controller 1048) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., controller 141, and controller 1048) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

The controller (e.g., controller 141, and controller 1048) is typically a hardware device programmed with computer program instructions to produce a special purpose computer. For example, when programmed to perform the methods described herein, the controller typically acts as a special purpose computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with an infusion tube and a fluid reservoir, the apparatus comprising:
   an infusion pump configured to be coupled to the infusion tube and the fluid reservoir, the infusion pump comprising:
      an upstream valve;
      a downstream valve;
      a pressing surface disposed between the upstream and downstream valves and configured to press on the infusion tube when the infusion pump is coupled to the infusion tube;
      a pressure sensor configured to measure pressure within the infusion tube; and
      a controller configured to:
         in response to measured pressure measured while the upstream valve is closed and the downstream valve is open, determine that there is an occlusion in the infusion tube downstream of the downstream valve, and
         in response to the determination that there is an occlusion, toggle the upstream valve and the downstream valve, the toggling comprising:
            (a) while the upstream valve remains closed, isolating a segment of the infusion tube between the upstream and downstream valves by closing the downstream valve;
            (b) subsequently, while the downstream valve remains closed, causing infusion fluid to flow upstream toward the fluid reservoir by opening the upstream valve, thereby reducing pressure in the isolated segment of the infusion tube;
            (c) subsequently, while the downstream valve remains closed, closing the upstream valve; and
            (d) subsequently, while the upstream valve remains closed, causing infusion fluid to flow upstream toward the upstream valve by opening the downstream valve, thereby reducing pressure downstream of the downstream valve.

2. The apparatus according to claim 1, wherein the controller is configured to perform the toggling of the upstream valve and the downstream valve while the infusion tube is partially squeezed by the pressing surface.

3. The apparatus according to claim 1, wherein the pressure sensor is positioned between the upstream valve and the downstream valve.

4. The apparatus according to claim 1, wherein the controller is further configured to:
   withhold generating an alert indicative of the occlusion in response to determining that there is an occlusion in the infusion tube; and
   subsequently to the toggling, generate an alert indicating to a user of the infusion pump that there is an occlusion in the infusion tube.

5. The apparatus according to claim 1, wherein the controller is configured to repeat the toggling a plurality of times, thereby reducing pressure that is in the infusion tube due to the occlusion.

6. The apparatus according to claim 5, wherein the controller is configured to stop the toggling after a predetermined number of toggling cycles.

7. The apparatus according to claim 6, wherein the controller is further configured to set the predetermined number of toggling cycles based on the measured pressure indicative of the occlusion.

8. The apparatus according to claim 5, wherein the controller is configured to stop the toggling after a predetermined amount of time.

9. The apparatus according to claim 8, wherein the controller is further configured to set the predetermined amount of time based on the measured pressure indicative of the occlusion.

10. The apparatus according to claim 5, wherein the controller is further configured to generate an alert indicating to a user of the infusion pump that there is an occlusion in the infusion tube, and wherein the controller is configured to repeat the toggling a plurality of times prior to generating the alert.

11. The apparatus according to claim 10, wherein the controller is configured to repeat the toggling at least two times prior to generating the alert.

12. The apparatus according to claim 10, wherein the controller is configured to repeat the toggling up to 100 times prior to generating the alert.

13. The apparatus according to claim 5, wherein the controller is configured to:
   (a) using the pressure sensor, repeatedly measure the pressure in the infusion tube during the toggling, and
   (b) regulate the toggling in response to the repeated measuring of the pressure.

14. The apparatus according to claim 13, wherein the controller is configured to stop toggling when at least a threshold pressure decrease, due to the toggling, is detected by the repeated measuring of the pressure.

15. The apparatus according to claim 13, wherein the controller is configured to stop the toggling when a pressure value detected during the repeated measuring of the pressure passes below a threshold.

16. The apparatus according to claim 15, wherein the controller is further configured to set the threshold based on the measured pressure indicative of the occlusion.

17. The apparatus according to claim 15, wherein the controller is further configured to, subsequently to stopping the toggling when the pressure passes below the threshold, assess that the infusion tube is no longer occluded in response to detecting a further reduction in pressure in the infusion tube.

18. The apparatus according to claim 15, wherein the controller is configured to stop the toggling based on an amount of time of the toggling, even if the pressure value detected during the repeated measuring of the pressure does not pass below the threshold.

19. The apparatus according to claim 15, wherein the controller is configured to stop the toggling based on a number of toggling cycles, even if the pressure value detected during the repeated measuring of the pressure does not pass below the threshold.

20. The apparatus according to claim 19, wherein the controller is configured to stop the toggling after fewer than 100 toggling cycles, even if the pressure value detected during the repeated measuring of the pressure does not pass below the threshold.

* * * * *